(12) United States Patent
Prechtel et al.

(10) Patent No.: US 8,715,244 B2
(45) Date of Patent: May 6, 2014

(54) EXTENSIBLE INTERNAL BOLSTER FOR A MEDICAL DEVICE

(75) Inventors: Ericka Prechtel, Salt Lake City, UT (US); David L. Thorne, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 266 days.

(21) Appl. No.: 12/831,644

(22) Filed: Jul. 7, 2010

(65) Prior Publication Data

US 2011/0009828 A1 Jan. 13, 2011

Related U.S. Application Data

(60) Provisional application No. 61/223,562, filed on Jul. 7, 2009.

(51) Int. Cl.
*A61M 5/32* (2006.01)
(52) U.S. Cl.
USPC .......................... 604/177; 604/175; 604/910
(58) Field of Classification Search
USPC ......................................... 604/175–179, 910
See application file for complete search history.

(56) References Cited

U.S. PATENT DOCUMENTS

| | | |
|---|---|---|
| 574,387 A | 1/1897 | Buckler |
| 611,357 A | 9/1898 | Dembinski |
| 966,696 A | 8/1910 | Merrill |
| 1,390,564 A | 9/1921 | Knorr |
| 1,713,267 A | 5/1929 | Crowley |
| 1,719,428 A | 7/1929 | Friedman |
| 2,029,553 A | 2/1936 | Bartischi et al. |
| 2,230,226 A | 2/1941 | Auzin |
| 2,280,892 A | 4/1942 | Cowles |
| 2,433,480 A | 12/1947 | Rendich |
| 2,497,633 A | 2/1950 | Shapiro et al. |
| 2,719,747 A | 10/1955 | Layne |

(Continued)

FOREIGN PATENT DOCUMENTS

| | | |
|---|---|---|
| EP | 0930083 A2 | 7/1999 |
| EP | 2060293 A1 | 5/2009 |

(Continued)

OTHER PUBLICATIONS

PCT/US2010/041192 filed Jul. 7, 2010 Search Report dated Sep. 20, 2010.

(Continued)

*Primary Examiner* — Aarti B Berdichevsky
*Assistant Examiner* — Rebecca E Eisenberg
(74) *Attorney, Agent, or Firm* — Rutan & Tucker, LLP

(57) ABSTRACT

An internal bolster for use securing a medical device, such as a feeding tube, within a body of a patient is disclosed. In one embodiment, a feeding tube includes an internal bolster, comprising one or more bolster arms that each include a first end hingedly connected to a distal end of the medical device and a free second end. The bolster arms are selectively deployable between a first position wherein the bolster arms are substantially in-line with an axis of feeding tube, and a second position wherein the bolster arms are substantially deflected from the axis of the feeding tube to enable securement of the feeding tube within a stoma or other opening defined in the body. Various means for selectively moving the bolster arms between the first and second positions are disclosed. Related methods of use are also disclosed.

24 Claims, 24 Drawing Sheets

(56) References Cited

U.S. PATENT DOCUMENTS

| | | |
|---|---|---|
| 2,891,689 A | 6/1959 | Gould |
| 3,111,930 A | 11/1963 | Zipper |
| D198,453 S | 6/1964 | Weichselbaum |
| 3,241,514 A | 3/1966 | Grimland |
| 3,293,663 A | 12/1966 | Cronin |
| 3,341,417 A | 9/1967 | Sinaiko |
| 3,397,699 A | 8/1968 | Kohl |
| 3,518,428 A | 6/1970 | Ring |
| 3,529,633 A | 9/1970 | Vailancourt |
| 3,543,759 A | 12/1970 | McWhorter |
| 3,592,197 A | 7/1971 | Cohen |
| 3,643,358 A | 2/1972 | Morderosian |
| 3,724,882 A | 4/1973 | Dehar |
| 3,829,904 A | 8/1974 | Ling et al. |
| 3,831,583 A | 8/1974 | Edmunds, Jr. et al. |
| 3,840,009 A | 10/1974 | Michaels et al. |
| 3,891,997 A | 7/1975 | Herbert |
| 3,915,162 A | 10/1975 | Miller |
| 3,915,171 A | 10/1975 | Shermeta |
| 3,919,724 A | 11/1975 | Sanders et al. |
| 3,922,726 A | 12/1975 | Trentani et al. |
| 3,951,147 A | 4/1976 | Tucker et al. |
| 4,016,885 A | 4/1977 | Bruner |
| 4,027,391 A | 6/1977 | Samis |
| 4,035,653 A | 7/1977 | Karasko |
| 4,043,338 A | 8/1977 | Homm et al. |
| 4,043,346 A | 8/1977 | Mobley et al. |
| 4,062,573 A | 12/1977 | Fleischer |
| 4,121,108 A | 10/1978 | Manor |
| 4,123,806 A | 11/1978 | Amstutz et al. |
| 4,134,407 A | 1/1979 | Elam |
| 4,143,893 A | 3/1979 | Fleischer |
| 4,168,586 A | 9/1979 | Samis |
| 4,177,815 A | 12/1979 | Patel |
| 4,190,040 A | 2/1980 | Schulte |
| 4,190,057 A | 2/1980 | Hill et al. |
| 4,194,122 A | 3/1980 | Mitchell et al. |
| 4,202,349 A | 5/1980 | Jones |
| 4,222,374 A | 9/1980 | Sampson et al. |
| 4,227,293 A | 10/1980 | Taylor |
| 4,233,964 A | 11/1980 | Jefferts et al. |
| 4,245,639 A | 1/1981 | La Rosa |
| 4,274,006 A | 6/1981 | Caine |
| 4,349,498 A | 9/1982 | Ellis et al. |
| 4,361,153 A | 11/1982 | Slocum et al. |
| 4,366,708 A | 1/1983 | Warihashi |
| 4,370,982 A | 2/1983 | Reilly |
| 4,398,542 A | 8/1983 | Cunningham et al. |
| 4,405,305 A | 9/1983 | Stephen et al. |
| 4,406,567 A | 9/1983 | Samis |
| 4,425,119 A | 1/1984 | Berglund |
| 4,431,426 A | 2/1984 | Groshong et al. |
| 4,445,896 A | 5/1984 | Gianturco |
| 4,450,592 A | 5/1984 | Niederer et al. |
| 4,450,985 A | 5/1984 | Beard |
| 4,453,928 A | 6/1984 | Steiger |
| 4,456,011 A | 6/1984 | Warnecke |
| 4,469,483 A | 9/1984 | Becker et al. |
| 4,494,545 A | 1/1985 | Slocum et al. |
| 4,506,676 A | 3/1985 | Duska |
| 4,529,635 A | 7/1985 | Sheldon |
| 4,535,757 A | 8/1985 | Webster, Jr. |
| 4,543,088 A | 9/1985 | Bootman et al. |
| 4,549,879 A | 10/1985 | Groshong et al. |
| 4,559,046 A | 12/1985 | Groshong et al. |
| 4,571,749 A | 2/1986 | Fischell |
| 4,576,595 A | 3/1986 | Aas et al. |
| 4,583,917 A | 4/1986 | Shah |
| 4,592,747 A | 6/1986 | Pool |
| 4,606,347 A | 8/1986 | Fogarty et al. |
| 4,608,965 A | 9/1986 | Anspach, Jr. et al. |
| 4,612,877 A | 9/1986 | Hayes et al. |
| 4,617,015 A | 10/1986 | Foltz |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,643,472 A | 2/1987 | Schukei et al. |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,666,433 A | 5/1987 | Parks |
| 4,668,221 A | 5/1987 | Luther |
| 4,671,796 A | 6/1987 | Groshong et al. |
| 4,672,979 A | 6/1987 | Pohndorf |
| 4,673,394 A | 6/1987 | Fenton, Jr. et al. |
| 4,684,365 A | 8/1987 | Reinicke |
| 4,685,447 A | 8/1987 | Iversen et al. |
| 4,685,901 A | 8/1987 | Parks |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,163 A | 10/1987 | Parks |
| 4,701,166 A | 10/1987 | Groshong et al. |
| 4,704,103 A | 11/1987 | Stober et al. |
| 4,710,174 A | 12/1987 | Moden et al. |
| 4,718,894 A | 1/1988 | Lazorthes |
| 4,728,894 A | 3/1988 | Yoda et al. |
| 4,729,706 A | 3/1988 | Peterson et al. |
| 4,743,231 A | 5/1988 | Kay et al. |
| 4,744,788 A | 5/1988 | Mercer, Jr. |
| 4,746,158 A | 5/1988 | Fields |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,798,592 A | 1/1989 | Parks |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,832,687 A | 5/1989 | Smith, III |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,438 A | 9/1989 | Gauderer et al. |
| 4,863,470 A | 9/1989 | Carter |
| 4,872,483 A | 10/1989 | Shah |
| 4,886,501 A | 12/1989 | Johnston et al. |
| 4,892,518 A | 1/1990 | Cupp et al. |
| 4,904,241 A | 2/1990 | Bark |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,944,732 A | 7/1990 | Russo |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 4,994,034 A | 2/1991 | Botich et al. |
| 5,007,900 A | 4/1991 | Picha et al. |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,071,405 A | 12/1991 | Piontek et al. |
| 5,073,166 A | 12/1991 | Parks et al. |

(56) References Cited

U.S. PATENT DOCUMENTS

| | | |
|---|---|---|
| 5,084,015 A | 1/1992 | Moriuchi |
| 5,085,216 A | 2/1992 | Henley, Jr. et al. |
| 5,092,849 A | 3/1992 | Sampson |
| 5,094,496 A | 3/1992 | King, Sr. |
| 5,108,317 A | 4/1992 | Beinhaur et al. |
| 5,108,377 A | 4/1992 | Cone et al. |
| 5,111,310 A | 5/1992 | Parker et al. |
| 5,112,301 A | 5/1992 | Fenton, Jr. et al. |
| 5,112,303 A | 5/1992 | Pudenz et al. |
| 5,112,310 A | 5/1992 | Grobe |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,163,949 A | 11/1992 | Bonutti |
| 5,167,629 A | 12/1992 | Vertenstein et al. |
| 5,167,633 A | 12/1992 | Mann et al. |
| 5,167,638 A | 12/1992 | Felix et al. |
| 5,171,228 A | 12/1992 | McDonald |
| 5,176,653 A | 1/1993 | Metals |
| 5,176,662 A | 1/1993 | Bartholomew et al. |
| 5,178,423 A | 1/1993 | Combeau |
| 5,178,612 A | 1/1993 | Fenton, Jr. |
| 5,185,003 A | 2/1993 | Brethauer |
| 5,189,690 A | 2/1993 | Samuel |
| 5,190,529 A | 3/1993 | McCrory et al. |
| 5,193,106 A | 3/1993 | DeSena |
| 5,195,122 A | 3/1993 | Fabian |
| 5,195,123 A | 3/1993 | Clement |
| 5,201,715 A | 4/1993 | Masters |
| 5,203,771 A | 4/1993 | Melker et al. |
| 5,203,773 A | 4/1993 | Green |
| 5,203,777 A | 4/1993 | Lee |
| 5,213,574 A | 5/1993 | Tucker |
| 5,215,537 A | 6/1993 | Lynn et al. |
| 5,218,970 A | 6/1993 | Turnbull et al. |
| 5,222,499 A | 6/1993 | Allen et al. |
| D337,637 S | 7/1993 | Tucker |
| 5,224,938 A | 7/1993 | Fenton, Jr. |
| 5,234,438 A | 8/1993 | Semrad |
| 5,234,454 A | 8/1993 | Bangs |
| 5,248,302 A | 9/1993 | Patrick et al. |
| 5,255,670 A | 10/1993 | Lomholt |
| 5,263,930 A | 11/1993 | Ensminger |
| 5,273,529 A | 12/1993 | Idowu |
| 5,275,610 A | 1/1994 | Eberbach |
| 5,279,564 A | 1/1994 | Taylor |
| 5,281,205 A | 1/1994 | McPherson |
| 5,290,263 A | 3/1994 | Wigness et al. |
| 5,295,658 A | 3/1994 | Atkinson et al. |
| 5,299,253 A | 3/1994 | Wessels |
| 5,306,240 A | 4/1994 | Berry |
| 5,308,325 A | 5/1994 | Quinn et al. |
| 5,309,863 A | 5/1994 | Leeb, Jr. |
| 5,309,906 A | 5/1994 | LaBombard |
| 5,312,337 A | 5/1994 | Flaherty et al. |
| 5,318,545 A | 6/1994 | Tucker |
| 5,320,100 A | 6/1994 | Herweck et al. |
| 5,324,262 A | 6/1994 | Fischell et al. |
| 5,328,480 A | 7/1994 | Melker et al. |
| 5,332,398 A | 7/1994 | Miller et al. |
| 5,336,194 A | 8/1994 | Polaschegg et al. |
| 5,338,398 A | 8/1994 | Szwejkowski et al. |
| 5,342,321 A | 8/1994 | Potter |
| 5,350,360 A | 9/1994 | Ensminger et al. |
| 5,352,204 A | 10/1994 | Ensminger |
| 5,360,407 A | 11/1994 | Leonard et al. |
| 5,365,967 A | 11/1994 | Moore |
| 5,383,223 A | 1/1995 | Inokuchi |
| 5,383,233 A | 1/1995 | Russell |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,397,329 A | 3/1995 | Allen |
| 5,399,168 A | 3/1995 | Wadsworth, Jr. et al. |
| 5,399,173 A | 3/1995 | Parks et al. |
| 5,403,290 A | 4/1995 | Noble |
| 5,405,329 A | 4/1995 | Durand |
| 5,405,402 A | 4/1995 | Dye et al. |
| 5,411,491 A | 5/1995 | Goldhardt et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,429,605 A | 7/1995 | Richling et al. |
| 5,431,661 A | 7/1995 | Koch |
| 5,439,444 A | 8/1995 | Andersen et al. |
| 5,456,698 A | 10/1995 | Byland et al. |
| 5,458,572 A | 10/1995 | Campbell et al. |
| 5,458,583 A | 10/1995 | McNeely et al. |
| 5,462,528 A | 10/1995 | Roewer |
| 5,462,561 A | 10/1995 | Voda |
| 5,470,314 A | 11/1995 | Walinsky |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,514,112 A | 5/1996 | Chu et al. |
| 5,520,632 A | 5/1996 | Leveen et al. |
| 5,522,961 A | 6/1996 | Leonhardt |
| 5,527,277 A | 6/1996 | Ensminger et al. |
| 5,527,280 A | 6/1996 | Goelz |
| 5,527,307 A | 6/1996 | Srisathapat et al. |
| 5,531,684 A | 7/1996 | Ensminger et al. |
| 5,549,657 A | 8/1996 | Stern et al. |
| D373,418 S | 9/1996 | Szpak |
| 5,556,381 A | 9/1996 | Ensminger et al. |
| 5,556,385 A | 9/1996 | Andersen |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,624,413 A | 4/1997 | Markel et al. |
| 5,632,729 A | 5/1997 | Cai et al. |
| 5,637,102 A | 6/1997 | Tolkoff et al. |
| 5,638,832 A | 6/1997 | Singer et al. |
| 5,647,627 A | 7/1997 | Baessler |
| 5,647,855 A | 7/1997 | Trooskin |
| 5,662,612 A | 9/1997 | Niehoff |
| 5,676,146 A | 10/1997 | Scarborough |
| 5,681,280 A | 10/1997 | Rusk et al. |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,718,692 A | 2/1998 | Schon et al. |
| 5,720,734 A | 2/1998 | Copenhaver et al. |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,749,852 A | 5/1998 | Schwab et al. |

(56) References Cited

U.S. PATENT DOCUMENTS

| | | |
|---|---|---|
| 5,758,667 A | 6/1998 | Slettenmark |
| 5,762,631 A | 6/1998 | Klein |
| 5,769,823 A | 6/1998 | Otto |
| 5,773,552 A | 6/1998 | Hutchings et al. |
| 5,776,111 A | 7/1998 | Tesio |
| 5,776,188 A | 7/1998 | Shepherd et al. |
| 5,792,104 A | 8/1998 | Speckman et al. |
| 5,792,116 A | 8/1998 | Berg et al. |
| 5,810,789 A | 9/1998 | Powers et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,924 A | 11/1998 | Kelliher et al. |
| 5,836,935 A | 11/1998 | Ashton et al. |
| 5,840,063 A | 11/1998 | Flaherty |
| 5,843,069 A | 12/1998 | Butler et al. |
| 5,853,394 A | 12/1998 | Tolkoff et al. |
| 5,860,960 A | 1/1999 | Quinn |
| 5,868,702 A | 2/1999 | Stevens et al. |
| 5,882,353 A | 3/1999 | VanBeek et al. |
| 5,895,424 A | 4/1999 | Steele, Sr. et al. |
| 5,906,596 A | 5/1999 | Tallarida |
| 5,908,414 A | 6/1999 | Otto et al. |
| 5,910,128 A | 6/1999 | Quinn |
| 5,913,998 A | 6/1999 | Butler et al. |
| 5,916,263 A | 6/1999 | Goicoechea et al. |
| 5,925,017 A | 7/1999 | Kriesel et al. |
| 5,925,030 A | 7/1999 | Gross et al. |
| 5,928,197 A | 7/1999 | Niehoff |
| 5,931,829 A | 8/1999 | Burbank et al. |
| 5,935,107 A | 8/1999 | Taylor et al. |
| 5,941,855 A | 8/1999 | Picha et al. |
| 5,944,023 A | 8/1999 | Johnson et al. |
| 5,944,688 A | 8/1999 | Lois |
| 5,944,712 A | 8/1999 | Frassica et al. |
| 5,944,732 A | 8/1999 | Raulerson et al. |
| 5,947,953 A | 9/1999 | Ash et al. |
| 5,951,512 A | 9/1999 | Dalton |
| 5,951,522 A | 9/1999 | Rosato et al. |
| 5,954,687 A | 9/1999 | Baudino |
| 5,957,890 A | 9/1999 | Mann et al. |
| 5,968,011 A | 10/1999 | Larsen et al. |
| 5,970,162 A | 10/1999 | Kawashima |
| 5,988,719 A | 11/1999 | Lavender |
| 5,989,216 A | 11/1999 | Johnson et al. |
| 5,989,239 A | 11/1999 | Finch et al. |
| 5,993,473 A | 11/1999 | Chan et al. |
| 5,997,503 A | 12/1999 | Willis et al. |
| 5,997,524 A | 12/1999 | Burbank et al. |
| 5,997,546 A | 12/1999 | Foster et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,027,518 A | 2/2000 | Gaber |
| 6,033,379 A | 3/2000 | Barra et al. |
| 6,033,389 A | 3/2000 | Cornish |
| 6,039,712 A | 3/2000 | Fogarty et al. |
| 6,045,536 A | 4/2000 | Meier et al. |
| 6,050,987 A | 4/2000 | Rosenbaum |
| 6,066,112 A | 5/2000 | Quinn |
| 6,066,155 A | 5/2000 | Amann et al. |
| 6,077,243 A | 6/2000 | Quinn |
| 6,077,756 A | 6/2000 | Lin et al. |
| 6,086,555 A | 7/2000 | Eliasen et al. |
| 6,090,066 A | 7/2000 | Schnell |
| 6,102,884 A | 8/2000 | Squitieri |
| 6,113,572 A | 9/2000 | Gailey et al. |
| 6,113,579 A | 9/2000 | Eidenschink et al. |
| 6,120,492 A | 9/2000 | Finch et al. |
| 6,149,575 A | 11/2000 | Leonhardt |
| 6,161,033 A | 12/2000 | Kuhn |
| 6,171,298 B1 | 1/2001 | Matsuura et al. |
| 6,186,985 B1 | 2/2001 | Snow |
| 6,190,349 B1 | 2/2001 | Ash et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,203,570 B1 | 3/2001 | Baeke |
| 6,213,973 B1 | 4/2001 | Eliasen et al. |
| 6,221,042 B1 | 4/2001 | Adams |
| 6,228,063 B1 | 5/2001 | Aboul-Hosn |
| 6,228,088 B1 | 5/2001 | Miller et al. |
| 6,251,059 B1 | 6/2001 | Apple et al. |
| D445,175 S | 7/2001 | Bertheas |
| 6,264,631 B1 | 7/2001 | Willis et al. |
| 6,269,148 B1 | 7/2001 | Jessop et al. |
| 6,287,293 B1 | 9/2001 | Jones et al. |
| 6,290,677 B1 | 9/2001 | Arai et al. |
| 6,305,413 B1 | 10/2001 | Fischer et al. |
| D450,115 S | 11/2001 | Bertheas |
| 6,315,789 B1 | 11/2001 | Cragg |
| 6,319,244 B2 | 11/2001 | Suresh et al. |
| 6,332,874 B1 | 12/2001 | Eliasen et al. |
| 6,355,021 B1 | 3/2002 | Nielsen et al. |
| 6,356,782 B1 | 3/2002 | Sirimanne et al. |
| 6,360,636 B1 | 3/2002 | Elftmann |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,428,256 B2 | 8/2002 | Wieser |
| 6,432,080 B2 | 8/2002 | Pederson, Jr. et al. |
| 6,450,937 B1 | 9/2002 | Mercereau et al. |
| 6,453,185 B1 | 9/2002 | O'Keefe |
| 6,475,244 B2 | 11/2002 | Herweck et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,506,179 B1 | 1/2003 | Tiefenthal et al. |
| 6,527,754 B1 | 3/2003 | Tallarida et al. |
| 6,530,898 B1 | 3/2003 | Nimkar et al. |
| 6,537,255 B1 | 3/2003 | Raines |
| RE38,074 E | 4/2003 | Recinella et al. |
| 6,565,536 B1 * | 5/2003 | Sohn ............................ 604/174 |
| 6,565,594 B1 | 5/2003 | Herweck et al. |
| 6,582,395 B1 | 6/2003 | Burkett et al. |
| 6,582,418 B1 | 6/2003 | Verbeek et al. |
| 6,595,971 B1 | 7/2003 | von Dyck et al. |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |
| 6,632,217 B2 | 10/2003 | Harper et al. |
| 6,638,242 B2 | 10/2003 | Wilson et al. |
| 6,652,486 B2 | 11/2003 | Bialecki et al. |
| 6,666,853 B2 | 12/2003 | Chu et al. |
| 6,669,681 B2 | 12/2003 | Dudar et al. |
| 6,676,633 B2 | 1/2004 | Smith et al. |
| 6,682,519 B1 | 1/2004 | Schon |
| 6,695,832 B2 | 2/2004 | Schon et al. |
| 6,697,664 B2 | 2/2004 | Kienzle, III et al. |
| 6,702,336 B1 | 3/2004 | Chelchowski et al. |
| 6,705,316 B2 | 3/2004 | Blythe et al. |
| 6,705,320 B1 | 3/2004 | Anderson |
| 6,718,707 B2 | 4/2004 | Marshall |
| 6,719,721 B1 | 4/2004 | Okazaki et al. |
| 6,719,739 B2 | 4/2004 | Verbeek et al. |
| 6,719,749 B1 | 4/2004 | Schweikert et al. |
| 6,730,056 B1 | 5/2004 | Ghaem et al. |
| 6,732,734 B2 | 5/2004 | Ogushi et al. |
| 6,738,531 B1 | 5/2004 | Funahashi |
| D490,890 S | 6/2004 | Li |
| 6,749,574 B2 | 6/2004 | O'Keefe |
| 6,752,827 B2 | 6/2004 | Ross et al. |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,796,741 B1 | 9/2004 | DeVaull, III et al. |

(56) References Cited

U.S. PATENT DOCUMENTS

| | | |
|---|---|---|
| 6,826,257 B2 | 11/2004 | Sayre et al. |
| 6,852,106 B2 | 2/2005 | Watson et al. |
| 6,858,019 B2 | 2/2005 | McGuckin, Jr. et al. |
| 6,872,198 B1 | 3/2005 | Wilson et al. |
| 6,878,130 B2 | 4/2005 | Fournie et al. |
| 6,878,136 B2 | 4/2005 | Fleury et al. |
| 6,878,137 B2 | 4/2005 | Benchetrit |
| 6,881,211 B2 | 4/2005 | Schweikert et al. |
| 6,896,665 B2 | 5/2005 | Picha et al. |
| 6,916,307 B2 | 7/2005 | Willis et al. |
| 6,921,396 B1 | 7/2005 | Wilson et al. |
| 6,929,621 B2 | 8/2005 | Whitmore et al. |
| 6,949,084 B2 | 9/2005 | Marggi et al. |
| 6,960,222 B2 | 11/2005 | Vo et al. |
| 6,962,580 B2 | 11/2005 | Adams et al. |
| 6,976,980 B2 | 12/2005 | Brenner et al. |
| 6,994,315 B2 | 2/2006 | Ryan et al. |
| 6,997,909 B2 | 2/2006 | Goldberg |
| 6,997,914 B2 | 2/2006 | Smith et al. |
| 7,008,377 B2 | 3/2006 | Beane et al. |
| 7,008,412 B2 | 3/2006 | Maginot |
| 7,008,438 B2 | 3/2006 | O'Brien |
| 7,008,441 B2 | 3/2006 | Zucker |
| 7,016,456 B2 | 3/2006 | Basu et al. |
| 7,018,361 B2 | 3/2006 | Gillespie, Jr. et al. |
| 7,018,384 B2 | 3/2006 | Skakoon |
| 7,041,083 B2 | 5/2006 | Chu et al. |
| 7,044,942 B2 | 5/2006 | Jolly et al. |
| 7,056,316 B1 | 6/2006 | Burbank et al. |
| 7,060,050 B2 | 6/2006 | Kliem et al. |
| 7,070,587 B2 | 7/2006 | Meier |
| 7,070,591 B2 | 7/2006 | Adams et al. |
| 7,072,704 B2 | 7/2006 | Bucholz |
| 7,074,232 B2 | 7/2006 | Kanner et al. |
| 7,083,593 B2 | 8/2006 | Stultz |
| 7,083,595 B2 | 8/2006 | Chu et al. |
| 7,108,686 B2 | 9/2006 | Burke et al. |
| 7,123,690 B1 | 10/2006 | Brown et al. |
| 7,124,489 B2 | 10/2006 | Triebes et al. |
| 7,127,040 B2 | 10/2006 | Sayre et al. |
| 7,128,734 B1 | 10/2006 | Wilson et al. |
| 7,131,962 B1 | 11/2006 | Estabrook et al. |
| 7,140,769 B2 | 11/2006 | Kay |
| 7,186,238 B2 | 3/2007 | Elbert et al. |
| 7,191,011 B2 | 3/2007 | Cantlon |
| 7,198,631 B2 | 4/2007 | Kanner et al. |
| D542,414 S | 5/2007 | Atkins |
| 7,214,207 B2 | 5/2007 | Lynch et al. |
| 7,214,215 B2 | 5/2007 | Heinzerling et al. |
| 7,220,243 B2 | 5/2007 | Bonnette et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,252,469 B2 | 8/2007 | Zaluzec et al. |
| 7,252,649 B2 | 8/2007 | Sherry |
| 7,261,705 B2 | 8/2007 | Edoga et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside |
| 7,300,430 B2 | 11/2007 | Wilson et al. |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,442 S | 2/2008 | Blateri |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,341,284 B2 | 3/2008 | Mittersteiner et al. |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| 7,381,204 B2 | 6/2008 | Wilson et al. |
| 7,393,339 B2 | 7/2008 | Zawacki et al. |
| 7,396,060 B2 | 7/2008 | Huncovsky |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| 7,534,224 B2 | 5/2009 | Triebes et al. |
| 7,547,303 B2 | 6/2009 | DeLegge |
| D595,892 S | 7/2009 | Smith et al. |
| 7,563,025 B2 | 7/2009 | Kay |
| 7,582,072 B2 | 9/2009 | McMichael |
| 7,621,903 B2 | 11/2009 | DeLegge |
| 7,625,361 B2 | 12/2009 | Suzuki et al. |
| 7,628,775 B2 | 12/2009 | Adams et al. |
| 7,628,795 B2 | 12/2009 | Karwoski et al. |
| 7,713,251 B2 | 5/2010 | Tallarida et al. |
| 7,749,185 B2 | 7/2010 | Wilson et al. |
| 7,819,840 B2 | 10/2010 | Burnside et al. |
| 7,833,214 B2 | 11/2010 | Wilson et al. |
| 7,959,615 B2 | 6/2011 | Stats et al. |
| 8,100,884 B2 | 1/2012 | Schweikert et al. |
| 8,105,313 B2 | 1/2012 | Schweikert et al. |
| 8,206,347 B2 | 6/2012 | Burnside et al. |
| 2001/0016717 A1 | 8/2001 | Haarala et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0093199 A1 | 7/2002 | Le |
| 2002/0095205 A1 | 7/2002 | Edwin et al. |
| 2002/0138068 A1 | 9/2002 | Watson et al. |
| 2002/0173769 A1 | 11/2002 | Gray et al. |
| 2003/0028173 A1 | 2/2003 | Forsberg |
| 2003/0055454 A1 | 3/2003 | Zucker |
| 2003/0088213 A1 | 5/2003 | Schweikert et al. |
| 2003/0120260 A1 | 6/2003 | Chu et al. |
| 2003/0130627 A1 | 7/2003 | Smith et al. |
| 2003/0139812 A1 | 7/2003 | Garcia et al. |
| 2003/0181878 A1 | 9/2003 | Tallarida et al. |
| 2003/0191452 A1 | 10/2003 | Meglin et al. |
| 2003/0212385 A1 | 11/2003 | Brenner et al. |
| 2003/0225376 A1 | 12/2003 | Fournie et al. |
| 2004/0006329 A1 | 1/2004 | Scheu |
| 2004/0020462 A1 | 2/2004 | Sauler et al. |
| 2004/0039372 A1 | 2/2004 | Carmody |
| 2004/0041399 A1 | 3/2004 | Chelchowski et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0065333 A1 | 4/2004 | Wilson et al. |
| 2004/0073196 A1 | 4/2004 | Adams et al. |
| 2004/0087984 A1 | 5/2004 | Kupiecki et al. |
| 2004/0092863 A1 | 5/2004 | Raulerson et al. |
| 2004/0103518 A1 | 6/2004 | Triebes et al. |
| 2004/0106878 A1 | 6/2004 | Skujins et al. |
| 2004/0106891 A1 | 6/2004 | Langan et al. |
| 2004/0106899 A1 | 6/2004 | McMichael et al. |
| 2004/0106901 A1 | 6/2004 | Letson et al. |
| 2004/0122418 A1 | 6/2004 | Voorhees |
| 2004/0147874 A1 | 7/2004 | Kliem et al. |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0176743 A1 | 9/2004 | Morris et al. |
| 2004/0181235 A1 | 9/2004 | Daignault et al. |
| 2004/0193119 A1 | 9/2004 | Canaud et al. |
| 2004/0199129 A1 | 10/2004 | DiMatteo |
| 2004/0199220 A1 | 10/2004 | Cantlon |
| 2004/0204692 A1 | 10/2004 | Eliasen |

(56) References Cited

U.S. PATENT DOCUMENTS

| | | |
|---|---|---|
| 2004/0210237 A1 | 10/2004 | Ross et al. |
| 2004/0225254 A1 | 11/2004 | Tanaka et al. |
| 2004/0230204 A1 | 11/2004 | Wortley et al. |
| 2004/0254536 A1 | 12/2004 | Conlon et al. |
| 2004/0254537 A1 | 12/2004 | Conlon et al. |
| 2005/0027282 A1 | 2/2005 | Schweikert et al. |
| 2005/0038381 A1 | 2/2005 | McMichael |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0085765 A1 | 4/2005 | Voorhees |
| 2005/0096585 A1 | 5/2005 | Schon et al. |
| 2005/0113806 A1 | 5/2005 | De Carvalho et al. |
| 2005/0131352 A1 | 6/2005 | Conlon et al. |
| 2005/0148866 A1 | 7/2005 | Gunderson |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0187535 A1 | 8/2005 | Wilson et al. |
| 2005/0200122 A1 | 9/2005 | Mittersteiner et al. |
| 2005/0209573 A1 | 9/2005 | Brugger et al. |
| 2005/0215874 A1 | 9/2005 | Wang et al. |
| 2005/0228364 A1 | 10/2005 | Braga |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0267415 A1 | 12/2005 | Jacques |
| 2005/0277899 A1 | 12/2005 | Conlon et al. |
| 2005/0283119 A1 | 12/2005 | Uth et al. |
| 2006/0009783 A1 | 1/2006 | Rome et al. |
| 2006/0009788 A1 | 1/2006 | Freeman et al. |
| 2006/0015130 A1 | 1/2006 | Voorhees et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0095062 A1 | 5/2006 | Stephens |
| 2006/0100592 A1 | 5/2006 | Eliasen |
| 2006/0116648 A1 | 6/2006 | Hamatake |
| 2006/0135949 A1 | 6/2006 | Rome et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0224128 A1 | 10/2006 | Lurvey et al. |
| 2006/0224129 A1 | 10/2006 | Beasley et al. |
| 2006/0247584 A1 | 11/2006 | Sheetz et al. |
| 2006/0253076 A1 | 11/2006 | Butts et al. |
| 2006/0264898 A1 | 11/2006 | Beasley et al. |
| 2006/0276746 A1 | 12/2006 | Burnside et al. |
| 2007/0021771 A1 | 1/2007 | Oepen et al. |
| 2007/0049876 A1 | 3/2007 | Patton |
| 2007/0049960 A1 | 3/2007 | Stephens et al. |
| 2007/0055290 A1 | 3/2007 | Lober |
| 2007/0066964 A1 | 3/2007 | Atkins |
| 2007/0073250 A1 | 3/2007 | Schneiter |
| 2007/0078391 A1 | 4/2007 | Wortley et al. |
| 2007/0078396 A1 | 4/2007 | Feeley et al. |
| 2007/0078416 A1 | 4/2007 | Eliasen |
| 2007/0078432 A1 | 4/2007 | Halseth et al. |
| 2007/0078478 A1 | 4/2007 | Atkins et al. |
| 2007/0083156 A1 | 4/2007 | Muto et al. |
| 2007/0088259 A1 | 4/2007 | Chu et al. |
| 2007/0120683 A1 | 5/2007 | Flippen et al. |
| 2007/0123842 A1 | 5/2007 | Teague et al. |
| 2007/0149920 A1 | 6/2007 | Michels et al. |
| 2007/0149921 A1 | 6/2007 | Michels et al. |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0244426 A1 | 10/2007 | Hart et al. |
| 2007/0255209 A1 | 11/2007 | Crooms et al. |
| 2007/0255234 A1 | 11/2007 | Haase et al. |
| 2007/0265597 A1 | 11/2007 | Schweikert et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276356 A1 | 11/2007 | Downing et al. |
| 2007/0282274 A1 | 12/2007 | Chesnin |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0058730 A1 | 3/2008 | Melsheimer |
| 2008/0097409 A1 | 4/2008 | Stephens |
| 2008/0114308 A1 | 5/2008 | di Palma et al. |
| 2008/0138387 A1 | 6/2008 | Machiraju |
| 2008/0188897 A1 | 8/2008 | Krebs et al. |
| 2008/0208236 A1 | 8/2008 | Hobbs et al. |
| 2008/0214992 A1 | 9/2008 | Haarala et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0030426 A1 | 1/2009 | Zinn et al. |
| 2009/0035582 A1 | 2/2009 | Nakatani et al. |
| 2009/0105652 A1 | 4/2009 | Beal et al. |
| 2009/0112183 A1 | 4/2009 | Jacques |
| 2009/0118683 A1 | 5/2009 | Hanson et al. |
| 2009/0156928 A1 | 6/2009 | Evans et al. |
| 2009/0192435 A1 | 7/2009 | Gregersen |
| 2009/0204072 A1 | 8/2009 | Amin et al. |
| 2009/0204074 A1 | 8/2009 | Powers et al. |
| 2009/0221950 A1 | 9/2009 | Atkins |
| 2009/0221976 A1 | 9/2009 | Linden |
| 2009/0227862 A1 | 9/2009 | Smith et al. |
| 2009/0227951 A1 | 9/2009 | Powers et al. |
| 2009/0299377 A1 | 12/2009 | Bright |
| 2009/0318873 A1 | 12/2009 | Bailey |
| 2010/0004601 A1 | 1/2010 | Deckard |
| 2010/0010448 A1 | 1/2010 | Deckard |
| 2010/0042073 A1 | 2/2010 | Oster et al. |
| 2010/0057013 A1 | 3/2010 | Harada |
| 2010/0063512 A1 | 3/2010 | Braga et al. |
| 2010/0063513 A1 | 3/2010 | Braga et al. |
| 2010/0069743 A1 | 3/2010 | Sheetz et al. |
| 2010/0174291 A1 | 7/2010 | Atkins et al. |
| 2010/0185155 A1 | 7/2010 | McMichael et al. |
| 2010/0312192 A1 | 12/2010 | Fitzgerald et al. |
| 2011/0196341 A1 | 8/2011 | Howell |
| 2012/0053485 A1 | 3/2012 | Bloom |
| 2012/0059321 A1 | 3/2012 | Hammond et al. |
| 2012/0238959 A1 | 9/2012 | Thorne et al. |
| 2012/0245519 A1 | 9/2012 | Rotella et al. |

FOREIGN PATENT DOCUMENTS

| | | |
|---|---|---|
| EP | 2308547 A2 | 4/2011 |
| EP | 2451512 A1 | 5/2012 |
| GB | 2012595 A | 8/1979 |
| GB | 2103936 A | 3/1983 |
| JP | 2000-515797 T | 11/2000 |
| JP | 2006025948 A | 2/2006 |
| JP | 4988725 B2 | 8/2012 |
| JP | 2012192182 A | 10/2012 |
| JP | 5184512 | 4/2013 |
| JP | 2013-518697 A | 5/2013 |
| WO | 8600213 A1 | 1/1986 |
| WO | 9305730 A1 | 4/1993 |
| WO | 9701370 A1 | 1/1997 |
| WO | 9706845 A1 | 2/1997 |

(56) References Cited

FOREIGN PATENT DOCUMENTS

| | | | |
|---|---|---|---|
| WO | 9801182 | A1 | 1/1998 |
| WO | 9817337 | A1 | 4/1998 |
| WO | 9819730 | A1 | 5/1998 |
| WO | 9852631 | A1 | 11/1998 |
| WO | 9915220 | A1 | 4/1999 |
| WO | 0023137 | A1 | 4/2000 |
| WO | 0033901 | A1 | 6/2000 |
| WO | 0247549 | A1 | 6/2002 |
| WO | 02087492 | A1 | 11/2002 |
| WO | 2004004800 | A2 | 1/2004 |
| WO | 2004050009 | A1 | 6/2004 |
| WO | 2004071555 | A2 | 8/2004 |
| WO | 2004091434 | A2 | 10/2004 |
| WO | 2005037055 | A2 | 4/2005 |
| WO | 2006078915 | A2 | 7/2006 |
| WO | 2006096686 | A1 | 9/2006 |
| WO | 2006116438 | A2 | 11/2006 |
| WO | 2006130133 | A1 | 12/2006 |
| WO | 2006134100 | A1 | 12/2006 |
| WO | 2007037876 | A1 | 4/2007 |
| WO | 2007079024 | A2 | 7/2007 |
| WO | 2007087254 | A2 | 8/2007 |
| WO | 2007092210 | A1 | 8/2007 |
| WO | 2007094898 | A2 | 8/2007 |
| WO | 2007098771 | A2 | 9/2007 |
| WO | 2007109164 | A2 | 9/2007 |
| WO | 2007126645 | A2 | 11/2007 |
| WO | 2007136538 | A2 | 11/2007 |
| WO | 2008008126 | A2 | 1/2008 |
| WO | 2008019236 | A1 | 2/2008 |
| WO | 2008048361 | A1 | 4/2008 |
| WO | 2008063226 | A2 | 5/2008 |
| WO | 2008147760 | A1 | 12/2008 |
| WO | 2008157763 | A1 | 12/2008 |
| WO | 2009002839 | A1 | 12/2008 |
| WO | 2009012385 | A1 | 1/2009 |
| WO | 2009012395 | A1 | 1/2009 |
| WO | 2009015016 | A1 | 1/2009 |
| WO | 2009035582 | A1 | 3/2009 |
| WO | 2009046439 | A2 | 4/2009 |
| WO | 2009046725 | A1 | 4/2009 |
| WO | 2009108669 | A1 | 9/2009 |
| WO | 2009135141 | A1 | 11/2009 |
| WO | 2011005847 | A1 | 1/2011 |
| WO | 2011100310 | A2 | 8/2011 |

OTHER PUBLICATIONS

BARD Access Systems Mar. 21, 1995 Product Release to Market form for "M.R.I. Port with 8 Fr. ChronoFlexÒ Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit". Drawings included.

Biffi, R. et al. "Use of totally implantable central venous access ports for high-dose chemotherapy and peripheral blood stem cell transplantation: results of a monocentre series of 376 patients." Annals of Oncology 15:296-300, 2004.

Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.

Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.

Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.

Costa, Nancy, "More Than Skin Deep: An Overview of Iodinated Contrast Media.." Journal for the Association for Vascular Access, vol. 8, No. 4, 2003.

Costa, Nancy, "Understanding Contrast Media." Journal of Infusion Nursing, vol. 27, No. 5, Sep./Oct. 2004.

EP 06751411 filed Apr. 25, 2006 Office Action dated Sep. 2, 2008.

EP 99964086 filed Dec. 3, 1999 Office Action dated Dec. 15, 2005.

EP 99964086 filed Dec. 3, 1999 Office Action dated Mar. 1, 2005.

EP 99964086 filed Dec. 3, 1999 Office Action dated Mar. 30, 2005.

Extravasation of Radiologic Contrast, PA-PSRS Patient Safety Advisory, vol. 1 No. 3, Sep. 2004.

Extreme Access™ Bard Access Systems, Inc. Product Brochure, 2003.

Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.

Hou, Shaw-Min et al. "Comparisons of Outcomes and Survivals for Two Central Venous Access Port Systems." Journal of Surgical Oncology, 91:61-66, 2005.

Inamed Health, BioEnterics® LAP-BAND® "Adjustable Gastric Banding System" Product Brochure, Dec. 2003.

Johnson, Kathleen A., "Power Injectable Portal Systems." Journal of Radiology Nursing, vol. 28, Issue 1, Mar. 2009.

LaMaitre Vascular "Port Implantations: using the OptiLock Implantable Port," product information, available at http://www.lemaitre.com/specs.pop.asp, last accessed Apr. 2003, 14 pages.

LAP-BAND AP™ "System with Adjustable Gastric Banding system with OMNIFORM TN Design," Product Brochure, Jul. 2007, 16 pages.

LAP-BAND® System Access Port Fill Guide I, "9.75/10.0 cm LAP-BAND System vs. 11 cm LAP-BAND System: For Product Manufactured Prior to Jul. 2001" BioEnterics Corporation. Aug. 15, 2001.

LAP-BAND® "Adjustable Gastric Banding System" by BioEnterics Corporation, Product Brochure. 1999.

LAP-BANDÒSystem Fact Sheet. ã2007 Allergan, Inc.

MedComp "PortCT Technology", display at SIR Conference (Mar. 2006), Toronto, Canada.

Nucleus Cochlear Implant Systems; User Manual for the ESPrit 3G speech processor and accessories, Issue 2, Dec. 2001 http://www.cochlearamericas.com/PDFs/UserManualSprint.pdf.

Oct. 22, 2009 Declaration of Kelly Christian, Director of Product Development at BARD Access Systems, Inc, in support of and depicting a product on the market by Quinton Company approximately ten years prior to Oct. 22, 2009, 1 page.

PCT/US1999/028695 filed Dec. 3, 1999 International Preliminary Examination Report dated Apr. 21, 2001.

PCT/US1999/028695 filed Dec. 3, 1999 Search Report dated Apr. 11, 2000.

PCT/US2006/008022 filed Mar. 6, 2006 International Preliminary Report on Patentability dated Sep. 12, 2007.

PCT/US2006/008022 filed Mar. 6, 2006 Search Report dated Jul. 5, 2006.

PCT/US2006/008022 filed Mar. 6, 2006 Written Opinion dated Apr. 9, 2007.

PCT/US2006/015695 filed Apr. 25, 2006 Partial Search Report dated Sep. 29, 2006.

PCT/US2006/015695 filed Apr. 25, 2006 Search Report dated Jan. 11, 2007.

PCT/US2006/015695 filed Apr. 25, 2006 Written Opinion dated Jan. 11, 2007.

PCT/US2006/016056 filed Apr. 27, 2006 International Preliminary Report on Patentability dated Oct. 30, 2007.

PCT/US2006/016056 filed Apr. 27, 2006 Search Report dated Sep. 20, 2006.

PCT/US2006/016056 filed Apr. 27, 2006 Written Opinion dated Oct. 27, 2007.

PCT/US2006/049007 filed Dec. 21, 2006 International Preliminary Report on Patentability dated Jul. 1, 2008.

PCT/US2006/049007 filed Dec. 21, 2006 Search Report dated Oct. 1, 2007.

PCT/US2007/006776 filed Mar. 19, 2007 International Preliminary Report on Patentability dated Jan. 2, 2009.

PCT/US2007/006776 filed Mar. 19, 2007 Search Report, dated Dec. 18, 2007.

(56) References Cited

OTHER PUBLICATIONS

PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Oct. 29, 2008.
PCT/US2007/011015 filed May 7, 2007 Search Report dated Jun. 10, 2008.
PCT/US2007/011456 filed May 11, 2007 Search Report dated Aug. 28, 2008.
PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion mailed on Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report mailed on Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/062854 filed Oct. 30, 2009 International Search Report dated Dec. 10, 2009.
PCT/US2009/062854 filed Oct. 30, 2009 Written Opinion dated Dec. 10, 2009.
PCT/US2010/030256 filed Apr. 7, 2010 Search Report and Written Opinion dated Jun. 4, 2010.
PCT/US2011/049742 filed Aug. 30, 2011 International Search Report dated Dec. 22, 2011.
Port-A-Cath® P.A.S. PORT® Systems by Deltec, Product Specifications, 1999.
PORT-A-CATHÒ "Implantable Epidural, Aterial and Peritonial Access Systems" Internet Product Listing. http://web.archive.org/web/20001119035900/www.deltec.com/cPacspl.htm. Accessed Oct. 17, 2009.
PORT-A-CATHÒ "Many PORT-A-CATHÒ System Choices" Product Brochure. Ó1996 SIMS Deltec, Inc.
PORT-A-CATHÒ "Single-lumen Implantable Vascular Access Systems" Product Specifications. 2004 Smith Medical family of companies.
Rappolt, Richard T., et al. "Radiopaque Codification and X-ray Identification of Ingested Drugs." Ingestive Radiology, May-Jun. 1966.
Sandstede, Joern, "Pediatric CT," available online at www.multislice-ct.com, MultiSLICE-CT.com, version 02, May 2, 2003.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith, Lisa Hartkoph, "Implanted Ports, Computed Tomography, Power Injectors, and Catheter Rupture." Clinical Journal of Oncology Nursing, vol. 12 , No. 5. Oct. 2008.
Soloman, et al., "CIN Strategies: Anticipate, Manage, Prevent." Supplement to Imaging Economics, May 2007.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action mailed Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action mailed Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 10/888,817, filed Jul. 8, 2004 Advisory Action dated Aug. 26, 2009.
U.S. Appl. No. 10/888,817, filed Jul. 8, 2004 Final Office Action dated Jun. 18, 2009.
U.S. Appl. No. 10/888,817, filed Jul. 8, 2004 Non-Final Office Action dated Sep. 5, 2008.
U.S. Appl. No. 11/021,769, filed Dec. 21, 2004 Advisory Action dated May 22, 2012.
U.S. Appl. No. 11/021,769, filed Dec. 21, 2004 Final Office Action dated Feb. 13, 2012.
U.S. Appl. No. 11/021,769, filed Dec. 21, 2004 Advisory Action dated Feb. 22, 2011.
U.S. Appl. No. 11/021,769, filed Dec. 21, 2004 Final Office Action dated Dec. 7, 2010.
U.S. Appl. No. 11/021,769, filed Dec. 21, 2004 Final Office Action dated Jan. 21, 2009.
U.S. Appl. No. 11/021,769, filed Dec. 21, 2004 Final Office Action dated Mar. 3, 2010.
U.S. Appl. No. 11/021,769, filed Dec. 21, 2004 Non-Final Office Action dated Aug. 9, 2011.
U.S. Appl. No. 11/021,769, filed Dec. 21, 2004 Non-Final Office Action dated Jul. 31, 2009.
U.S. Appl. No. 11/021,769, filed Dec. 21, 2004 Non-Final Office Action dated Jul. 9, 2008.
U.S. Appl. No. 11/320,223, filed Dec. 28, 2005 Final Office Action dated Jun. 19, 2009.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Sep. 18, 2008.

(56) References Cited

OTHER PUBLICATIONS

U.S. Appl. No. 11/368,954, filed Mar. 6, 2006 Non-Final Office Action dated Jul. 21, 2009.
U.S. Appl. No. 11/368,954, filed Mar. 6, 2006 Final Office Action dated Jan. 27, 2010.
U.S. Appl. No. 11/368,954, filed Mar. 6, 2006 Preliminary Amendment dated Dec. 19, 2007.
U.S. Appl. No. 11/368,954, filed Mar. 6, 2006 Supplemental Non-final Office Action mailed Oct. 2, 2009.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Jan. 16, 2009.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action issued on Dec. 3, 2008.
U.S. Appl. No. 11/725,287, filed Mar. 19, 2007 Non-final Office Action issued on Jun. 12, 2009.
U.S. Appl. No. 11/725,287, filed Mar. 19, 2007 Non-final Office Action issued on Mar. 29, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/143,377, filed Jun. 20, 2008 Final Office Action mailed Oct. 19, 2009.
U.S. Appl. No. 12/143,377, filed Jun. 20, 2008 Non-final Office Action mailed Apr. 27, 2009.
U.S. Appl. No. 12/175,182, filed Jul. 17, 2008 Non-final Office Action mailed Sep. 3, 2009.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jun. 30, 2009.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.
U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annemarie Boswell as inventors.
Vergara, et al., "Adverse Reactions to Contrast Medica in CT: Effects of Temperature and Ionic Property." Radiology, vol. 199, No. 2, May 1996.
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
JP 2007-519438 filed Jun. 29, 2005 Decision to Grant dated Sep. 4, 2012.
JP 2007-519438 filed Jun. 29, 2005 Office Action dated Nov. 30, 2010.
Michaud, Laurent et al, Longevity of Balloon-Stabilized Skin-Level Gastrostomy Device, Journal of Pediatric Gastroenterology and Nutrition, 38: 426-429; Apr. 2004.
PCT/US11/24176 filed Feb. 9, 2011 International Preliminary Report on Patentability dated Oct. 11, 2012.
PCT/US11/24176 filed Feb. 9, 2011 International Search Report and Written Opinion dated Jul. 8, 2011.
PCT/US2005/023297 filed Jun. 29, 2005 International Preliminary Report on Patentability dated Jan. 9, 2007.
PCT/US2005/023297 filed Jun. 29, 2005 Search Report dated May 26, 2006.
PCT/US2005/023297 filed Jun. 29, 2005 Written Opinion dated May 26, 2006.
PCT/US2006/022020 filed Jun. 6, 2006 International Preliminary Report on Patentability dated Dec. 6, 2007.
PCT/US2006/022020 filed Jun. 6, 2006 Search Report dated Jan. 25, 2007.
PCT/US2006/022020 filed Jun. 6, 2006 Written Opinion dated Jan. 25, 2007.
PCT/US2010/041192 filed Jul. 7, 2010 International Search Report dated Sep. 20, 2010.
PCT/US2010/041192 filed Jul. 7, 2010 Written Opinion dated Sep. 20, 2010.
U.S. Appl. No. 11/127,662, filed May 12, 2005 Advisory Action dated May 16, 2008.
U.S. Appl. No. 11/127,662, filed May 12, 2005 Final Office Action dated Mar. 5, 2008.
U.S. Appl. No. 11/127,662, filed May 12, 2005 Final Office Action dated Mar. 6, 2007.
U.S. Appl. No. 11/127,662, filed May 12, 2005 Non-Final Office Action dated Aug. 9, 2007.
U.S. Appl. No. 11/127,662, filed May 12, 2005 Non-Final Office Action dated Jul. 9, 2008.
U.S. Appl. No. 11/127,662, filed May 12, 2005 Non-Final Office Action dated Oct. 17, 2006.
U.S. Appl. No. 11/422,559, filed Jun. 6, 2006 Final Office Action dated Apr. 2, 2009.
U.S. Appl. No. 11/422,559, filed Jun. 6, 2006 Non-Final Office Action dated Aug. 8, 2008.
U.S. Appl. No. 11/422,559, filed Jun. 6, 2006 Non-Final Office Action dated Jan. 6, 2010.
U.S. Appl. No. 11/422,559, filed Jun. 6, 2006 Notice of Allowance dated Jun. 24, 2010.
U.S. Appl. No. 11/629,724, filed Jun. 29, 2005 Non-Final Office Action dated Aug. 26, 2008.
U.S. Appl. No. 11/629,724, filed Jun. 29, 2005 Final Office Action dated Jan. 4, 2011.
U.S. Appl. No. 11/629,724, filed Jun. 29, 2005 Final Office Action dated May 4, 2010.
U.S. Appl. No. 11/629,724, filed Jun. 29, 2005 Non-Final Office Action dated Jul. 22, 2010.
U.S. Appl. No. 11/629,724, filed Jun. 29, 2005 Non-Final Office Action dated Oct. 2, 2009.
U.S. Appl. No. 11/738,979, filed Apr. 23, 2007 Final Office Action dated Jan. 13, 2012.
U.S. Appl. No. 11/738,979, filed Apr. 23, 2007 Advisory Action dated Jun. 18, 2009.
U.S. Appl. No. 11/738,979, filed Apr. 23, 2007 Final Office Action dated Apr. 16, 2009.
U.S. Appl. No. 11/738,979, filed Apr. 23, 2007 Final Office Action dated Jan. 25, 2010.
U.S. Appl. No. 11/738,979, filed Apr. 23, 2007 Non-Final Office Action dated Nov. 24, 2008.

(56) References Cited

OTHER PUBLICATIONS

U.S. Appl. No. 11/738,979, filed Apr. 23, 2007 Non-Final Office Action dated Oct. 9, 2009.
U.S. Appl. No. 12/265,102, filed Nov. 5, 2008 Advisory Action dated Apr. 3, 2012.
U.S. Appl. No. 12/265,102, filed Nov. 5, 2008 Final Office Action dated Jan. 13, 2012.
U.S. Appl. No. 12/265,102, filed Nov. 5, 2008 Non-Final Office Action dated Dec. 18, 2012.
U.S. Appl. No. 12/265,102, filed Nov. 5, 2008 Non-Final Office Action dated Jul. 29, 2011.
U.S. Appl. No. 12/902,987, filed Oct. 12, 2010 Final Office Action and Reasons for Allowance dated Dec. 22, 2011.
U.S. Appl. No. 12/902,987, filed Oct. 12, 2010 Notice of Allowance dated Dec. 22, 2011.
EP 11742731.0 filed Sep. 4, 2012 extended European Search Report dated Aug. 6, 2013.
U.S. Appl. No. 11/738,979, filed Apr. 23, 2007 Notice of Allowance dated Jun. 17, 2013.
U.S. Appl. No. 12/265,102, filed Nov. 5, 2008 Final Office Action dated Jun. 26, 2013.
U.S. Appl. No. 13/419,185, filed Mar. 13, 2012 Non-Final Office Action dated Sep. 3, 2013.

* cited by examiner

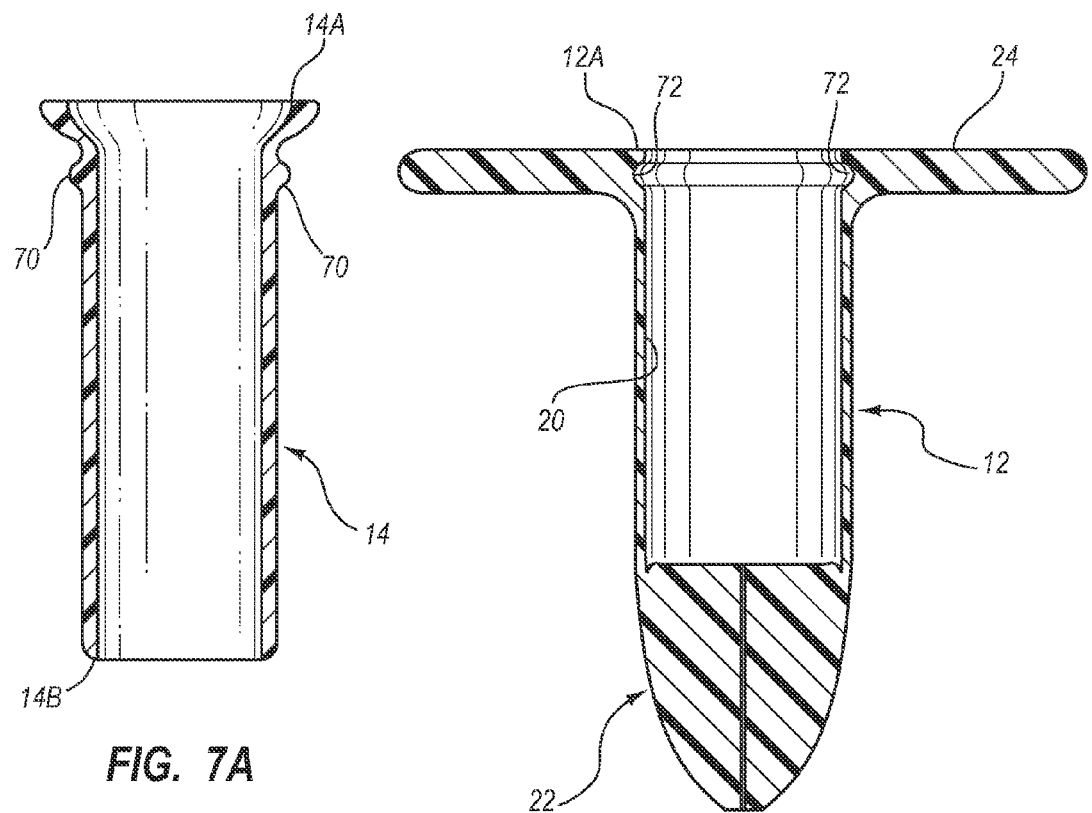
FIG. 7A
FIG. 7B
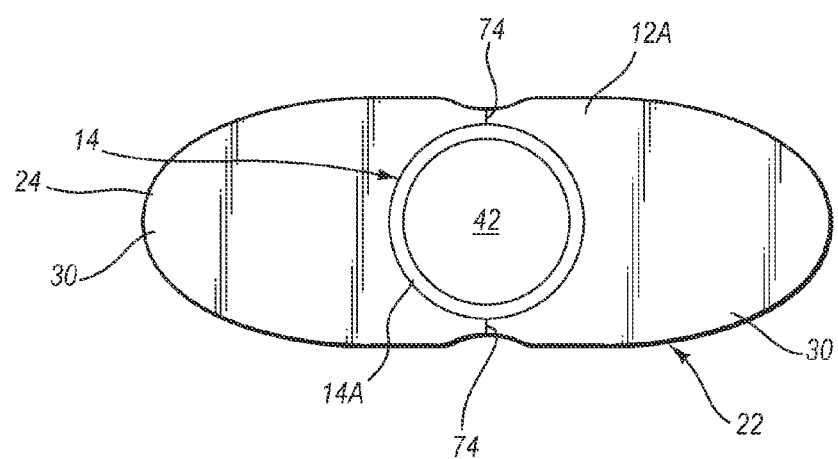
FIG. 7C

EXTENSIBLE INTERNAL BOLSTER FOR A MEDICAL DEVICE

CROSS-REFERENCE TO RELATED APPLICATIONS

This application claims the benefit of U.S. Provisional Patent Application No. 61/223,562, filed Jul. 7, 2009, and entitled "Feeding Device Including an Extensible Internal Bolster," which is incorporated herein by reference in its entirety.

BRIEF SUMMARY

Briefly summarized, embodiments of the present invention are directed to an internal bolster for use securing a medical device within a body of a patient. One example of a medical device includes a feeding tube for providing enteral nutrition to the patient, though many other medical devices can benefit from the principles to be depicted and described herein.

In one embodiment, the feeding tube includes an internal bolster, comprising one or more bolster arms that each include a first end hingedly connected to a distal end of the medical device and a free second end. The bolster arms are selectively deployable between a first position wherein the bolster arms are substantially in-line with an axis of feeding tube, and a second position wherein the bolster arms are substantially deflected from the axis of the feeding tube to enable securement of the feeding tube within a stoma or other opening defined in the body. Various means for selectively moving the bolster arms between the first and second positions are disclosed. Related methods of use for the internal bolster are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 7A-7C are various views of a feeding device such as that shown in FIG. 1A, including an interference locking mechanism in accordance with one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a feeding device placed within the body of a patient is considered a distal end of the catheter, while the feeding device end remaining outside the body is a proximal end of the catheter. Also, the words "including," "has," and "having," as used herein, including the claims, shall have the same meaning as the word "comprising."

FIGS. 1A-18E depict various features of embodiments of the present invention, which are generally directed to a selectively extensible or deployable internal bolster for use in anchoring a medical device, such as a feeding tube, within a body of a patient. The internal bolster is configured to selectively deploy from collapsed state to an expanded state so as to ease both insertion and removal of a device into or from a patient, such as via a stoma. This in turn reduces patient trauma and pain during placement and removal of the device.

Figure 1A:
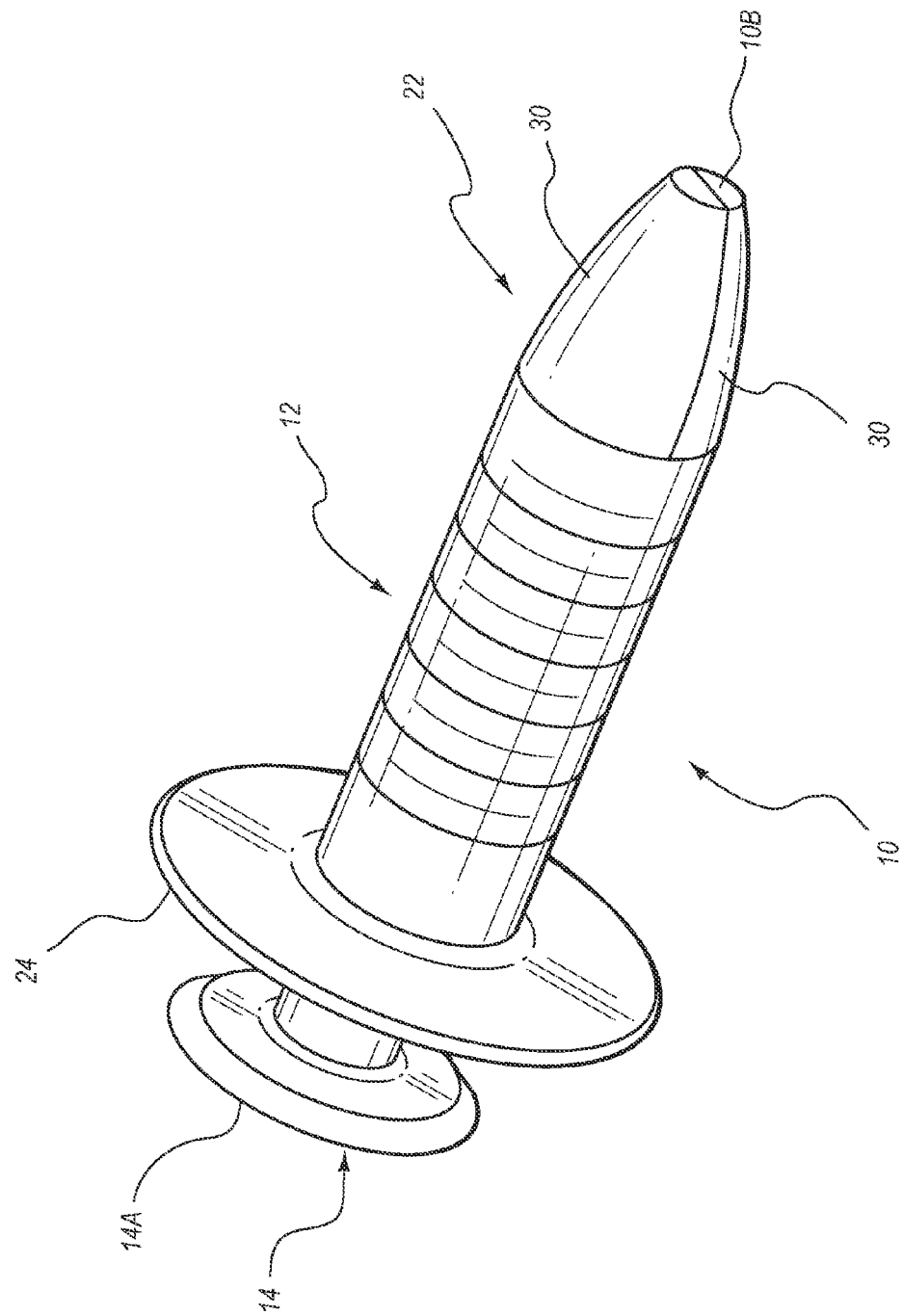
FIGS. 1A-1C are various views of a feeding device configured in accordance with one example embodiment of the present invention.
Figure 1B:
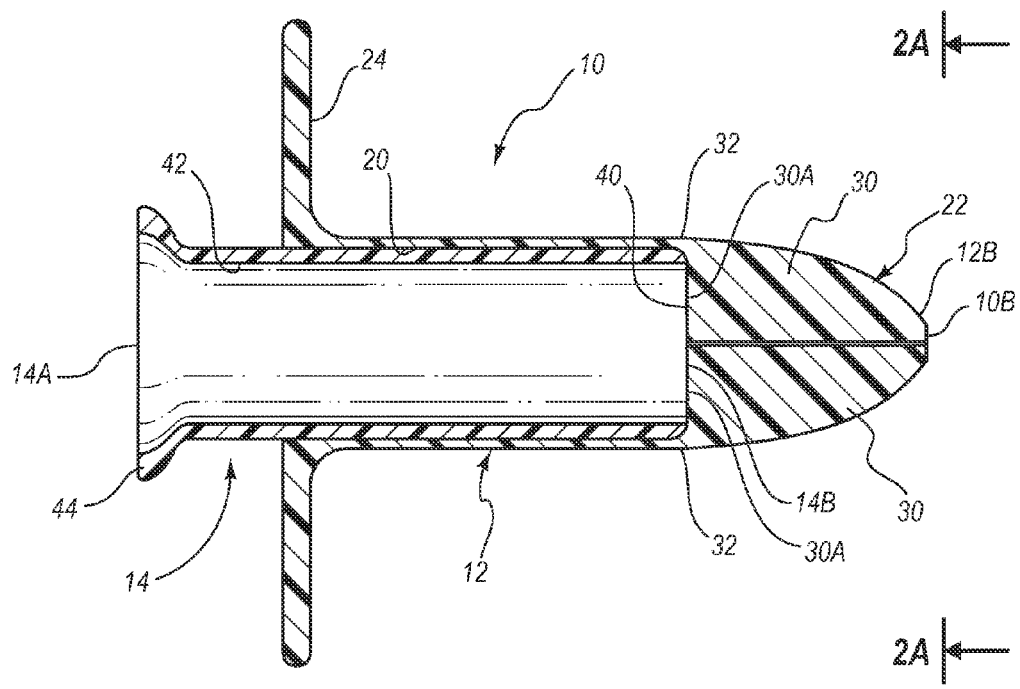
Figure 1C:
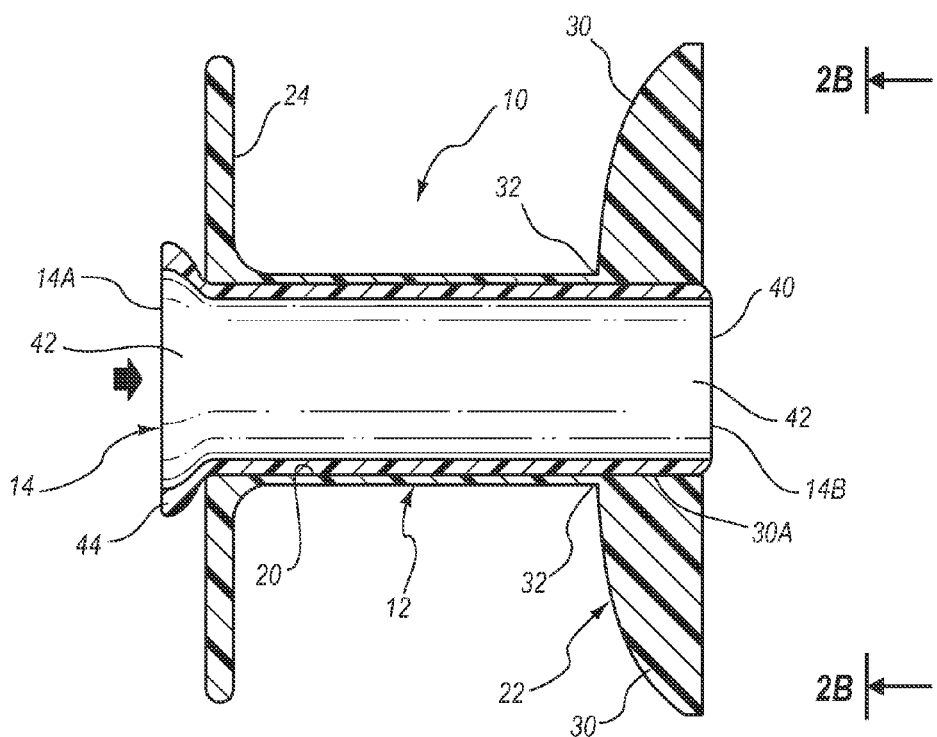

Reference is first made to FIGS. 1A-1C, which depict a feeding device, generally designated at 10, including an internal bolster configured in accordance with one example embodiment. The feeding device 10 generally includes an outer bolster tube 12 and an inner plunger 14. Including both a proximal end 14A and a distal end 14B, the plunger 14 is slidably received within an elongate cavity 20 defined by the bolster tube 12 via an opening to the cavity defined at a proximal end 12A thereof. A distal portion of the bolster tube 12 includes an internal bolster 22, while a flange 24 is included at a proximal portion of the bolster tube. The flange 24 can take one of many different configurations, including an annular shape, opposing tabs, etc.

In greater detail, the internal bolster 22 includes one or more bolster arms 30 that are each hingedly connected to a distal portion of the bolster tube 12 at a hinge point 32 via a living hinge or other suitable connection scheme. Each bolster arm 30 thus includes an end attached to the bolster tube 12 and a free end. So configured, the bolster arms 30 are pivotable about the hinge point 32 so as to be able to be selectively deployed from a first, un-deployed position shown in FIGS. 1A and 1B, i.e., the configuration for inserting or removing the feeding device via an opening or stoma defined in the patient such as to gain access to the stomach of the patient for example (similar to the insertion of the device shown in FIG. 11A), to a second, deployed position shown in FIG. 1C, i.e., the configuration wherein the bolster anchors the feeding device within the patient after insertion through the stoma (similar to the anchoring of the device shown in FIG. 11B). Note that when in the first, un-deployed position, the bolster arms 30 are contiguously disposed together in one embodiment to define an atraumatic tip for the feeding device 10 to assist in inserting the feeding device through the stoma or other opening defined in the tissue of a patient.

As best seen in FIGS. 1A and 1B the internal bolster 22, as positioned in the present embodiment, defines the distal end 10B of the feeding device 10. It is appreciated, however, that in other embodiments the internal bolster can be disposed at a point proximal to a distal end of the feeding tube or other device with which the internal bolster is included. As such, the discussion relating to the shape, design, and placement of the internal bolster embodiments described herein should not be considered limiting of the present invention in any way. Further, it is appreciated that, while shown in connection with a gastrostomy or feeding tube, the internal bolster can be included with insertable medical devices of a variety of types and configurations.

In the present embodiment, the plunger 14 of the feeding device 10 includes an engagement surface 40 at a distal end 14B thereof that is configured to actuate the bolster arms 30 of the internal bolster 22 when the plunger, received within the cavity 20 of the bolster tube 12, is pressed distally. In detail, a proximal end 14A of the plunger 14 can be manually pressed by a user to advance the plunger distally through the bolster tube cavity 20 during inner bolster actuation. The plunger proximal end 14A includes a first plunger stop 44 configured to limit distal insertion of the plunger 14 into the bolster tube cavity 20.

Distal movement of the plunger 14 with respect to the bolster tube 12 causes engagement of the plunger engagement surface 40 with a proximal base 30A of each bolster arm 30, which causes the bolster arms to hingedly pivot about the hinge point 32 and open, or deploy to the position shown in FIG. 1C. Thus, it is seen that in the un-deployed, or first, position shown in FIG. 1B, 2A a length of each bolster arm 30 is in-line, or aligned substantially parallel with a longitudinal axis of the bolster tube 12. So configured, the internal bolster 22 when in the un-deployed first position of FIG. 1B, 2A includes an outer diameter no larger than that of the bolster tube 12 to facilitate atraumatic insertion of the feeding tube 10 through the stoma. Correspondingly, in the deployed, or second, position of FIG. 1C, 2B each bolster arm opens radially outward such that the length of each bolster arm 30 is substantially non-parallel with respect to the longitudinal axis of the bolster tube 12, thus serving as a securement for preventing removal of the feeding tube 10 from a stoma or other hole through which the feeding tube is inserted. The deployability of the bolster arms 30 is selectively reversible such that withdrawal of the plunger 14 from engagement with the bases 30A of the bolster arms enables the bolster arms to return to the first position.

Note that in the present embodiment, the feeding tube is tubular and cross sectionally round; in other embodiments, however, a non-tubular or non-cross sectionally round medical device can also benefit from the principles described herein. Note further that the mode of attachment of the bolster arms to the bolster tube can include integral formation, molding or overmolding, mechanical fixation, adhesive attachment, etc.

Movement of the internal bolster 22 from the second deployed position to the first position, in preparation for removal of the feeding tube 10 for instance, is achieved via proximal movement of the plunger 14 with respect to the bolster tube 12. This movement separates the plunger engagement surface 40 from the bolster arm bases 30A, which allows the bolster arms 30 to pivot back to their un-deployed position shown in FIGS. 1B, 2A. This selective deployability of the internal bolster 22 enables the feeding device 10 to be readily inserted and removed from the patient. A channel 42 is defined by the plunger 14 therethrough so as to provide a pathway through which enteral nutrition can be provided to the patient. Valves, connectors, or other apparatus can be included with or attached to the feeding device to enable suitable access to the channel 42, and the channel can be modified from what is shown and described herein. Note that in the present embodiment, the bolster arms 30 substantially cover the distal opening feeding device 10 when in the first position (FIG. 1B), and that the distal opening is substantially uncovered when the bolster arms are in the second position (FIG. 1C).

It is thus seen that the plunger 14 described above serves as one example of a means for selectively moving the bolster arms between the first and second positions. It is appreciated that other methods and structures may be used for this purpose as may be appreciated by one skilled in the art and as seen in the discussion further below.

The bolster tube 12 and plunger 14 are sized to enable relative movement therebetween when the plunger is received within the cavity 20 of the bolster tube. Though configured as a sliding engagement in the present embodiment, the relative movement spoken of here can be implemented in other ways as well, including gear-teeth engagement, etc. The cross sectional profiles of both the bolster tube cavity 20 and the outer surface of the plunger 14 are round in the present embodiment. In other embodiments, other cross sectional shapes can be used, including square, pentagonal, oval, etc. In other embodiments, the plunger can be keyed to the bolster tube cavity so as to prevent relative rotation therebetween, if desired. In one embodiment, oil or other lubricants can be interposed between the bolster tube cavity 20 and the outer surface of the plunger 14 so as to ease relative movement therebetween.

Figure 3A:
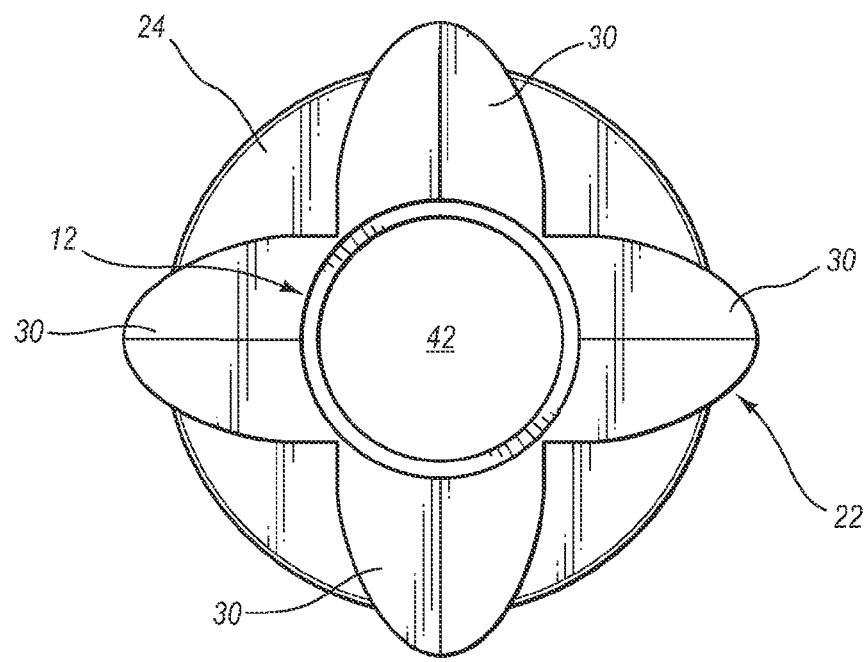
FIGS. 3A-3B are distal end views of example feeding devices such as that shown in FIG. 1A, including differing numbers of distal end internal bolster arms.
Figure 3B:
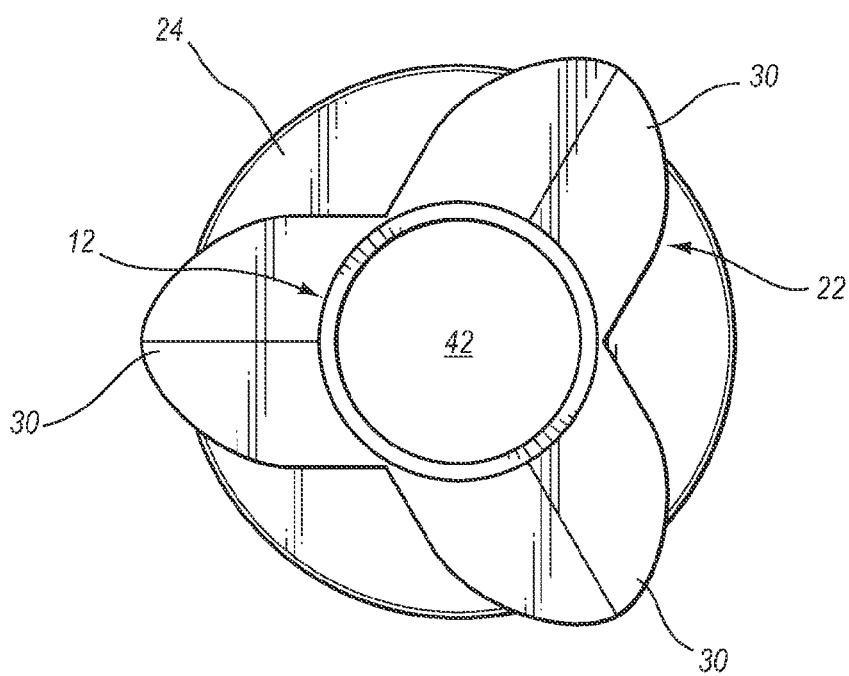

As indicated by FIGS. 3A and 3B, the number of bolster arms in the internal bolster 22 can include one, two, three, four, or more. Also, though shown here as contoured to assist in device insertion and removal, the bolster arms mutually or independently can define one of many shapes, including rectangular, round, bullet-shaped, triangular, etc. In the present embodiment both the bolster tube 12 and the plunger 14 include biocompatible materials, such as silicone for the bolster tube/bolster arms and acetyl homopolymer, e.g., an engineering plastic sold under the trademark DELRIN®, or other engineering plastic or suitable material for the plunger. As mentioned, the plunger can further include a valve for preventing inadvertent passage of material or air through the feeding device.

Note that, as indicated in FIGS. 1A-2B, the bolster arms 30 move in unison between the first and second positions. In other embodiments, however, the plunger can be configured such that the bolster arms move independently or at different stages of internal bolster deployment. This can be achieved, for instance, by including a staggered engagement surface on the distal end of the plunger or bolster arm base.

Figure 2A:
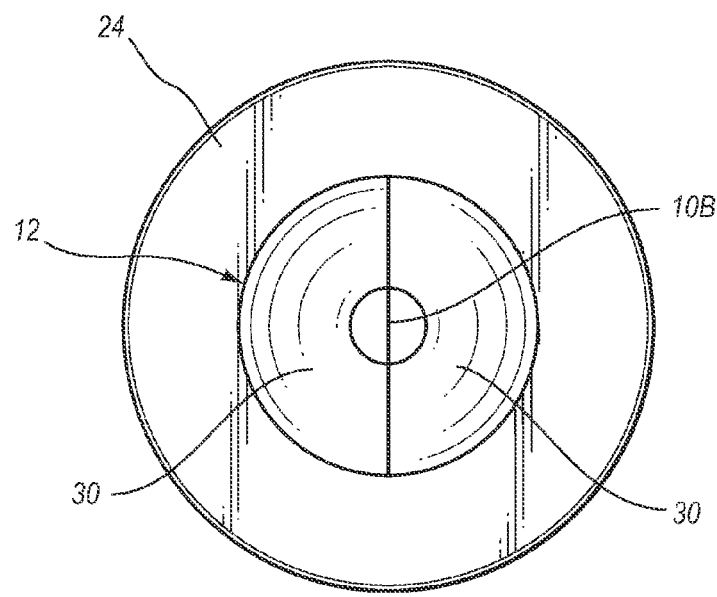
FIGS. 2A-2B are end views of the feeding device configurations shown in FIGS. 1B and 1C, respectively.
Figure 2B:
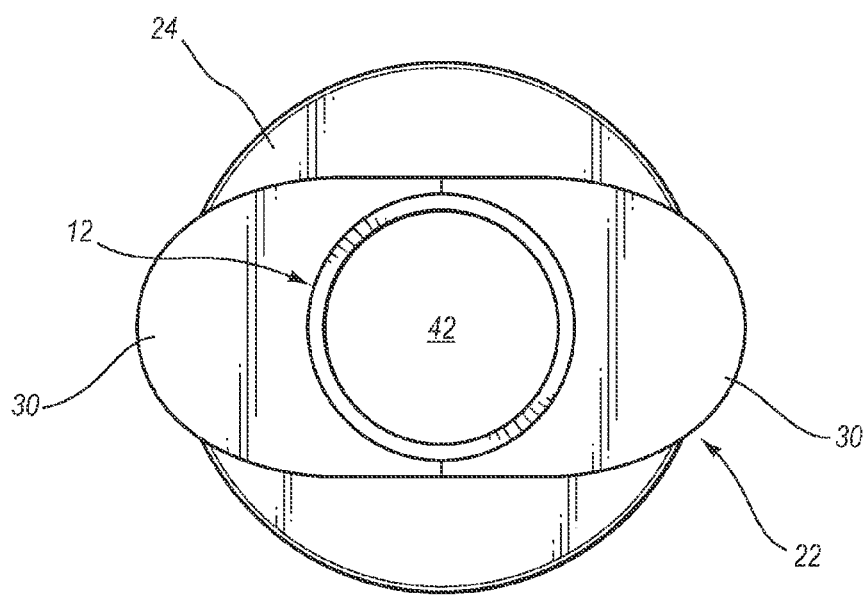
Figure 4A:
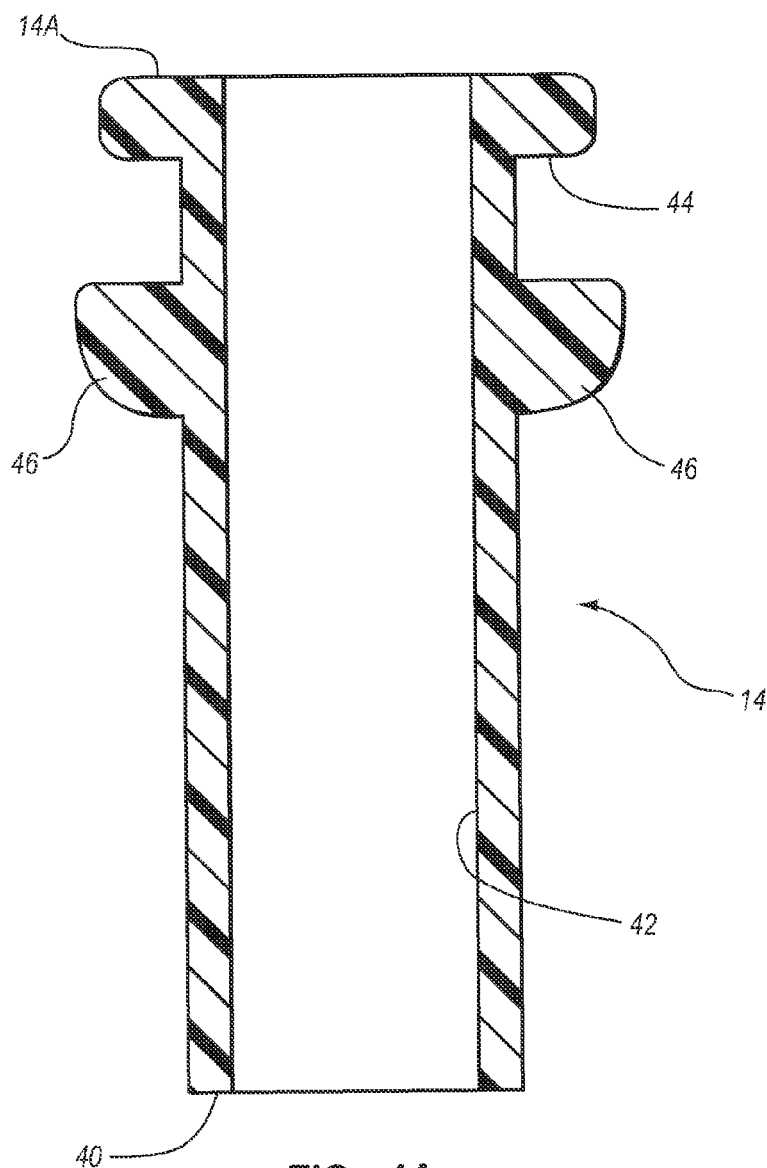
FIGS. 4A and 4B are cross sectional side and end views, respectively, of a plunger of the feeding device of FIG. 1A, according to one embodiment.
Figure 4B:
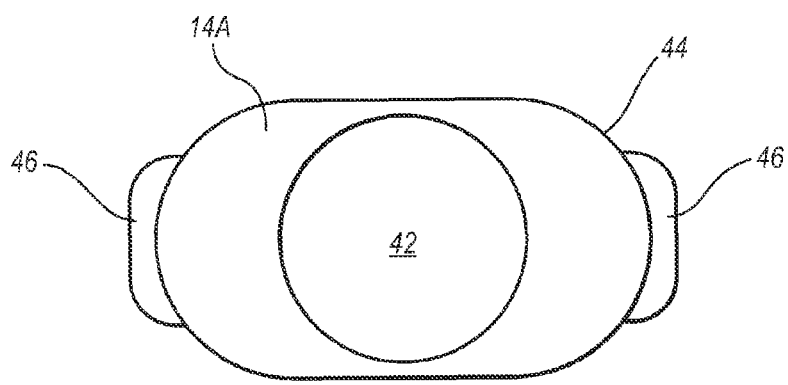

The feeding device 10 can include one of a variety of implementations for preventing unintended axial movement of the plunger 14 relative to the bolster tube 12 in order to prevent the bolster arms 30 from folding up from their deployed second position shown in FIG. 1C, 2B. One such implementation is shown in FIGS. 4A and 4B, wherein locking tabs 46 are included on an outer surface of a portion of the plunger 14 that is received by the bolster tube cavity 20. The tabs 14 are configured to be received into corresponding detents included on an inside surface of the bolster tube cavity 20 when the plunger 14 is pushed distally through the cavity in order to engage and spread open the bolster arms 30 of the internal bolster 22. Once received in the detents, the tabs 46 retain the plunger 14 within the bolster tube cavity 20 to lock it in place. Cutting of the bolster tube 12, for instance, can release the tabs 46 from the bolster tube detents in order to slide the plunger 14 relative to the bolster tube. Thus the tabs 14 and corresponding detents describe one example of means for locking axial plunger movement relative to the bolster tube 12 or other suitable device with which the plunger is included. It is appreciated that other methods and structures may be used for this purpose as may be appreciated by one skilled in the art and as seen in the below discussion.

FIGS. 7A-7C show a similar means for locking axial movement of the plunger 14 relative to the bolster tube 12, wherein an outer surface of the plunger 14 includes an annular knob 70 for engagement with a corresponding annular detent 72 defined by an inner surface of the bolster tube 12 in the cavity 20 when the plunger is inserted into the cavity to deploy the bolster arms 30. FIG. 7C is a proximal end view of the feeding device 10, showing the location of cut points 74 where the bolster tube 12 can be cut in order to separate the engagement between knob 70 and corresponding detent 72.

Figure 5:
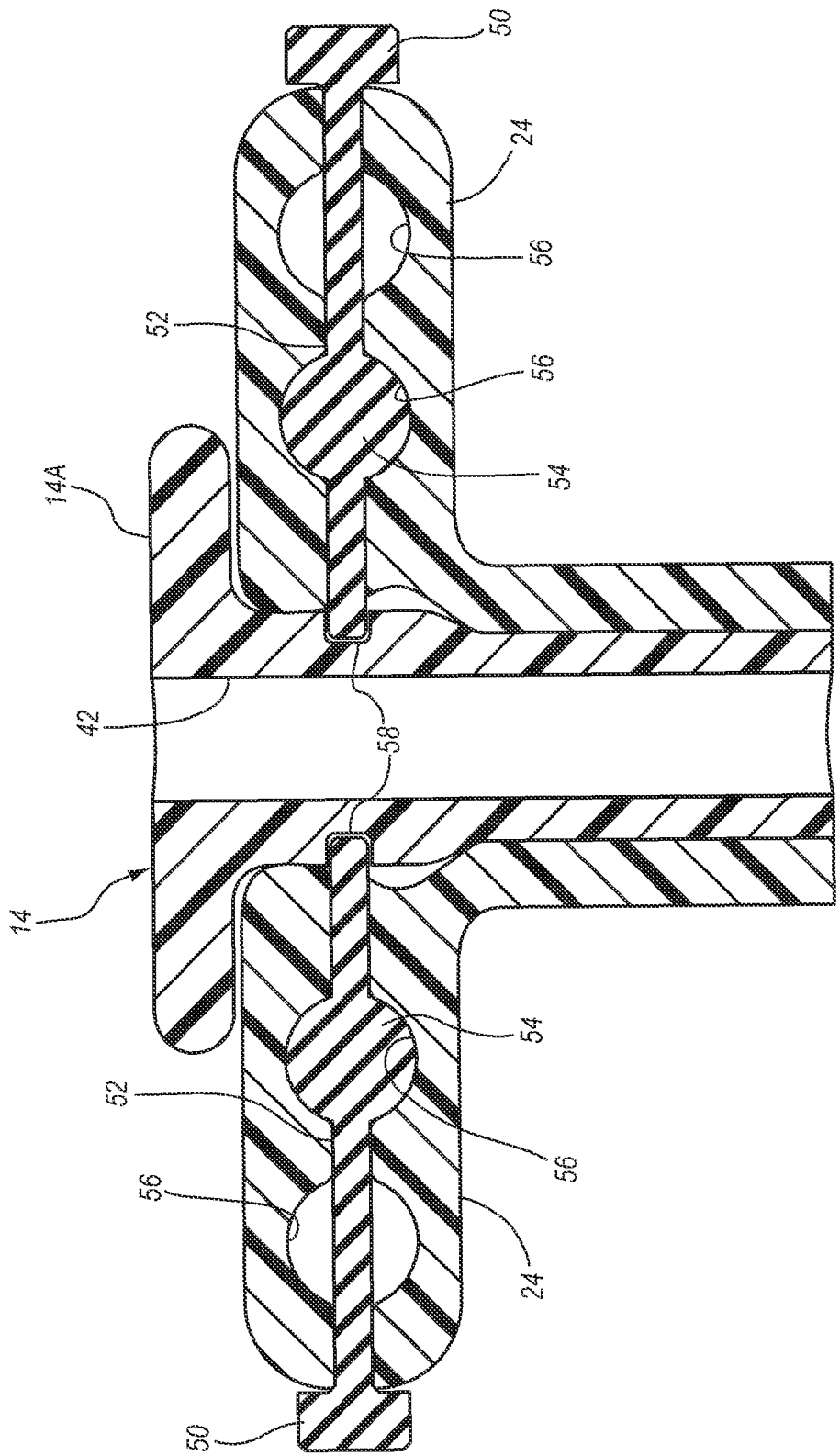
FIG. 5 is a cross sectional side view of a feeding device such as that shown in FIG. 1A, including a locking mechanism in accordance with one embodiment.

FIG. 5 shows another example of means for locking axial plunger movement relative to the bolster tube 12, wherein one or more pin channels 52 are defined by the bolster tube flange 24 and each configured for receiving a locking pin 50 therein. Each locking pin 50 includes a bump 54 that is selectively seatable in one of a plurality of detents 56 defined in the respective pin channel 52. Thus, each locking pin 50 can be selectively pushed or otherwise moved by a user between an outer one of the detents 56 to an inner detent, which action causes an inner end of the locking pin to engage a recess 58 or other suitable structure defined in an outer surface of the plunger 14, thus locking the plunger and bolster tube 12 together to prevent unintended movement therebetween when the plunger has been inserted sufficient to deploy the bolster arms 30 of the internal bolster 22. When relative plunger movement is again desired, the locking pin 50 can be pulled out to release the locking engagement and enable the plunger to be axially moved. Of course, this locking pin arrangement is merely an example of many other possible locking pin configurations that can be utilized in connection with the present feeding device. For instance, it is appreciated that a threaded locking pin and pin channel can be employed in one embodiment.

Figure 6A:
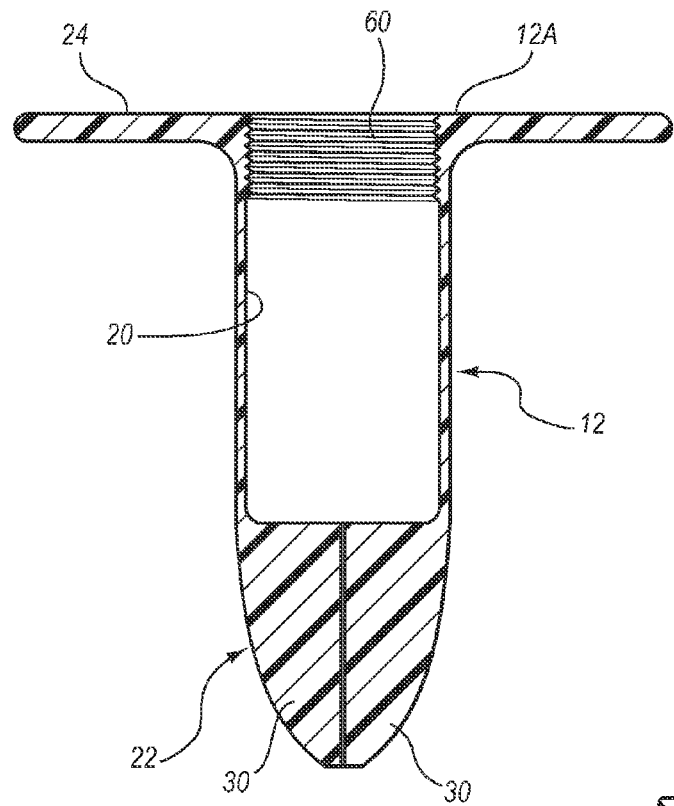
FIGS. 6A and 6B are cross sectional side views of a feeding device such as that shown in FIG. 1A, including a threaded locking mechanism in accordance with one embodiment.
Figure 6B:
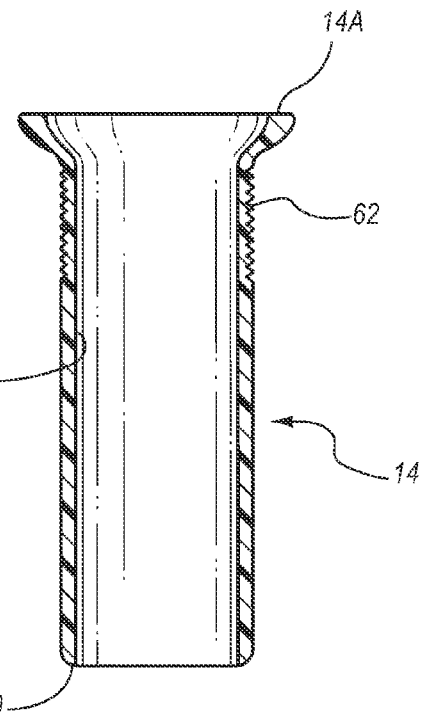

FIGS. 6A-6B depict yet another means for locking axial movement of the plunger 14 relative to the bolster tube 12, wherein corresponding threads 60 and 62 are included on an inner surface of the bolster tube cavity 20 and an outer surface of the plunger 14, respectively. So configured, the plunger 14 can be inserted into the bolster tube cavity 20 to actuate and deploy the internal bolster 22, then be rotated to threadingly engage its threads 62 with the threads 60 of the bolster tube 12 cavity, thus selectively locking the position of the two components. Should the insertion depth of the plunger 14 within the bolster tube cavity 20 need to be modified, the plunger can be selectively rotated clockwise or counter-clockwise as needed. When no rotation of the plunger 14 is made, axial movement of the plunger is prevented via engagement of the threads 60, 62.

Figure 8A:
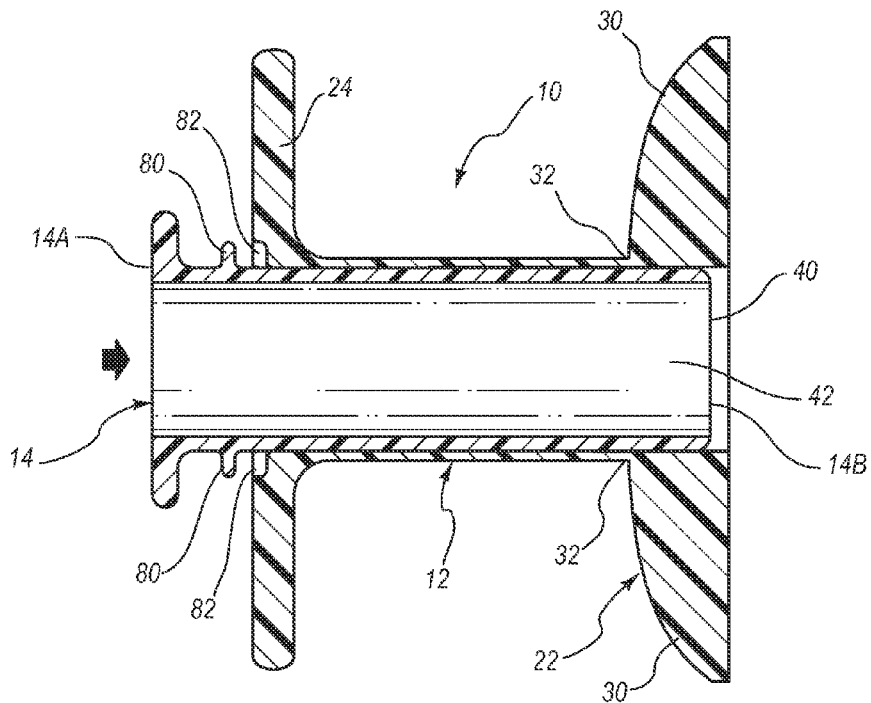
FIGS. 8A-8D are various views of a feeding device such as that shown in FIG. 1A, including a tab/slot locking mechanism in accordance with one embodiment.
Figures 8B, 8C:
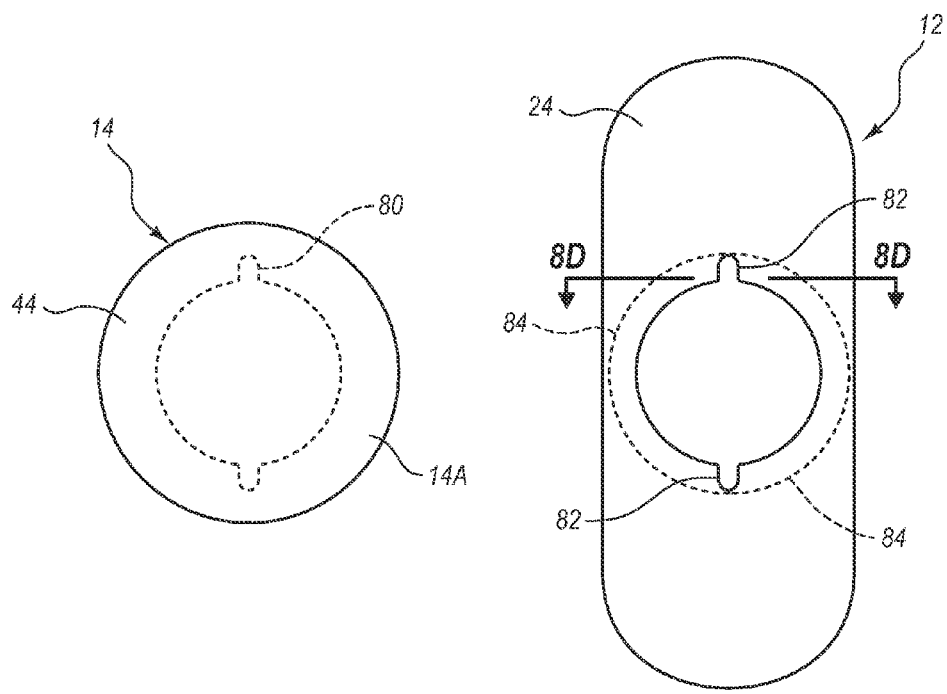
Figure 8D:
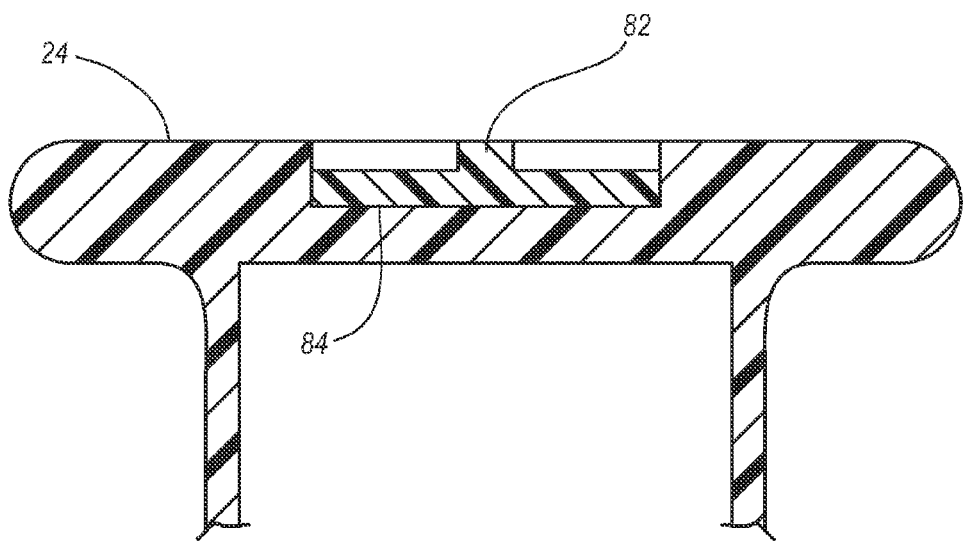

FIGS. 8A-8D show yet another means for locking axial movement of the plunger 14 relative to the bolster tube 12, wherein opposing tabs 80 are included on the plunger proximal end 14A for engagement with corresponding slots 82 defined by the bolster tube flange 24 when the plunger is inserted into the bolster tube cavity 20 in order to deploy the bolster arms 30 of the bolster tube internal bolster 22. FIGS. 8C and 8D show that each slot 82 defined in the bolster tube flange 24 is in communication with a channel 84 defined below the slots. The slots 82 enable the respective tabs 80 of the plunger 14 to be received therethrough and into the channel(s) 84 when the plunger is inserted into the bolster tube cavity 20 to deploy the internal bolster 22. Once the tabs are received into the channel(s) 84 via the slots 82, the plunger 14 is rotated about its longitudinal axis to cause the tabs to slide laterally within the channel(s) to a rest position such that the plunger is locked axially with respect to the bolster tube 12. The process can be reversed to free the plunger 14 from the bolster tube 12 in preparation of separation thereof. It is appreciated that the size, shape, and number of tabs, slots, and channels can vary from what is described herein.

Figure 8E:
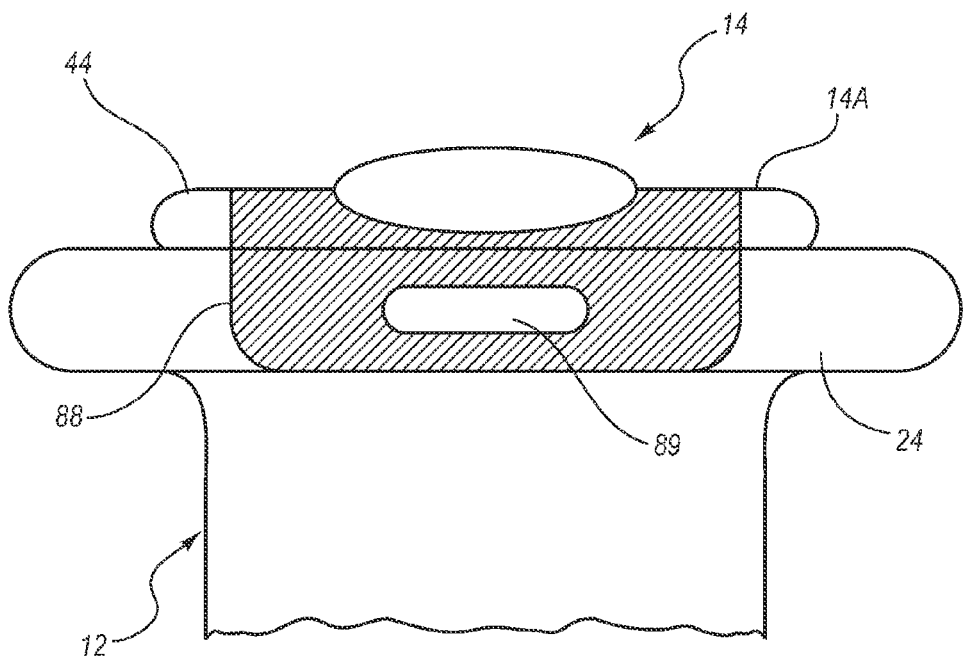
FIG. 8E is a side view of a retention cover for use with a feeding device in accordance with one embodiment.

FIG. 8E shows that an elastic cover 88 can be employed as yet another example of means for locking axial movement of the plunger 14 relative to the bolster tube 12, wherein the cover is slid over proximal portions of the plunger 14, e.g., the first plunger stop 44, and the bolster tube 12, e.g., the flange 24, to lock the two components together after deployment of the internal bolster 22. A knob 89 can be included on one of the components over which the cover 88 can be slid so as to keep the cover in place.

Figure 9A:
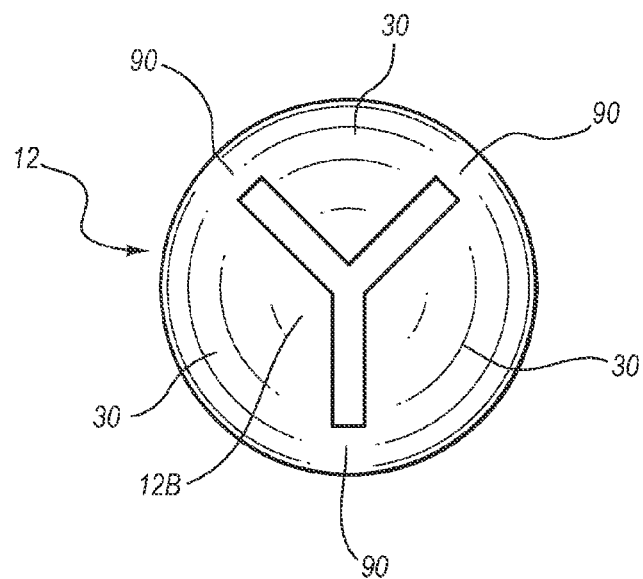
FIGS. 9A and 9B are end and side views, respectively, of a feeding device including webbing between bolster arms of the internal bolster.
Figure 9B:
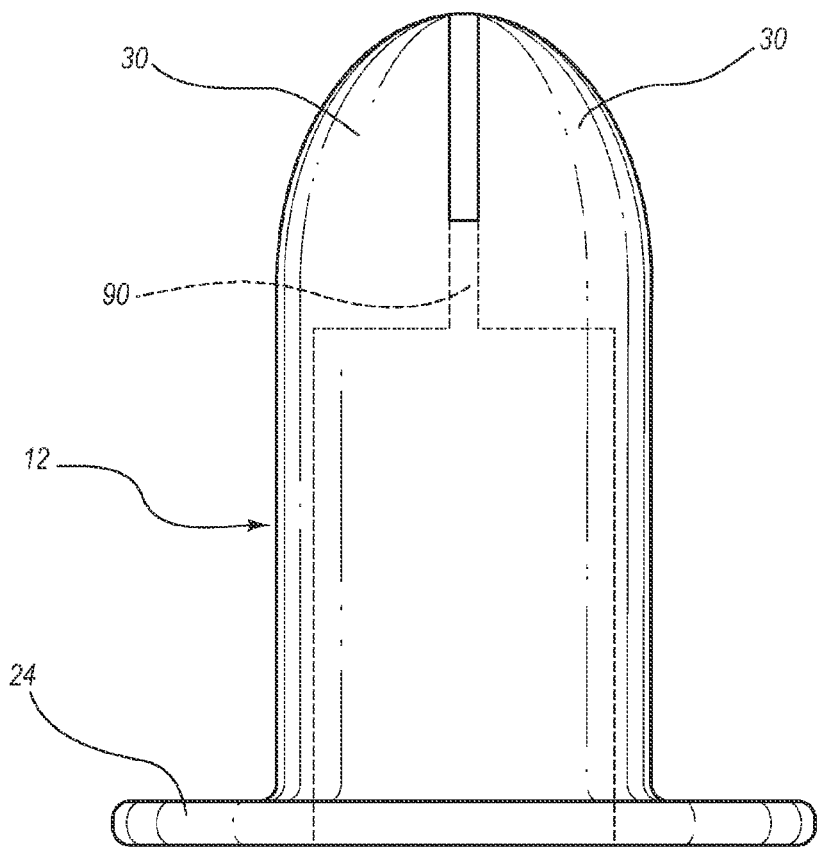
Figure 10:
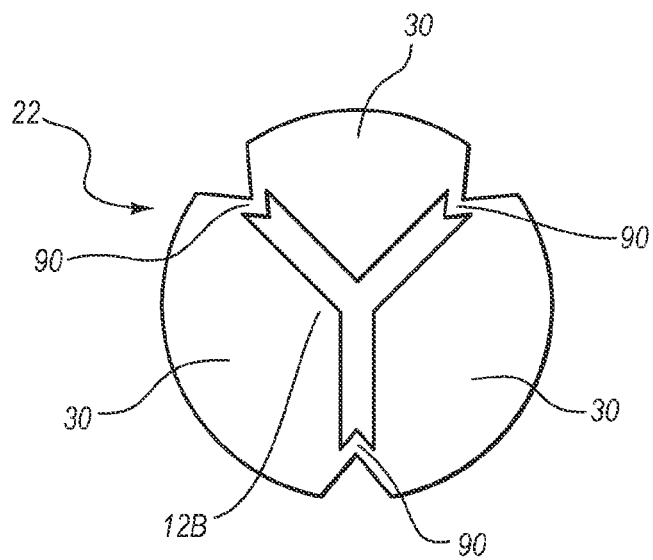
FIG. 10 is an end view of a feeding device including webbing between the bolster arms of the internal bolster according to one embodiment.

Reference is now made to FIGS. 9A and 9B, which show that in one embodiment webbing 90 is included between adjacent internal bolster arms 30. Formed of the same material from which the bolster arms 30 are formed, e.g., silicone, the webbing 90 helps in one embodiment to form a seal about the stoma when the internal bolster 22 is deployed into its expanded state (FIG. 1C). FIG. 10 shows that the webbing in one embodiment can be folded so as to provide relatively more webbing for ease in bolster arm expansion during internal bolster deployment. These and other modifications to the particular internal bolster configuration are thus contemplated.

Figure 11A:
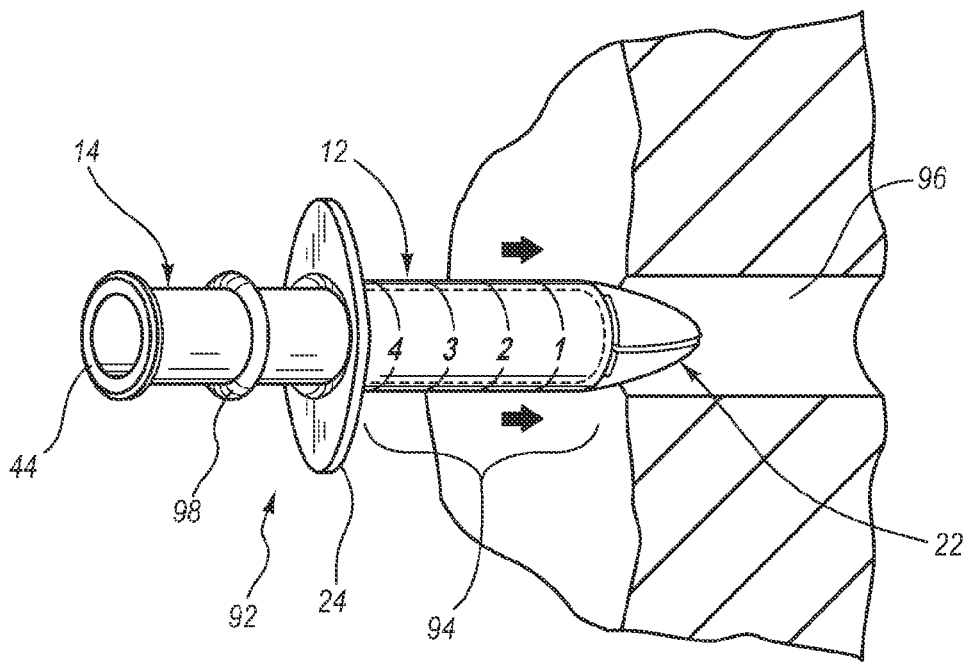
FIGS. 11A and 11B are side views of a feeding device including a stoma measuring system in accordance with one embodiment.
Figure 11B:
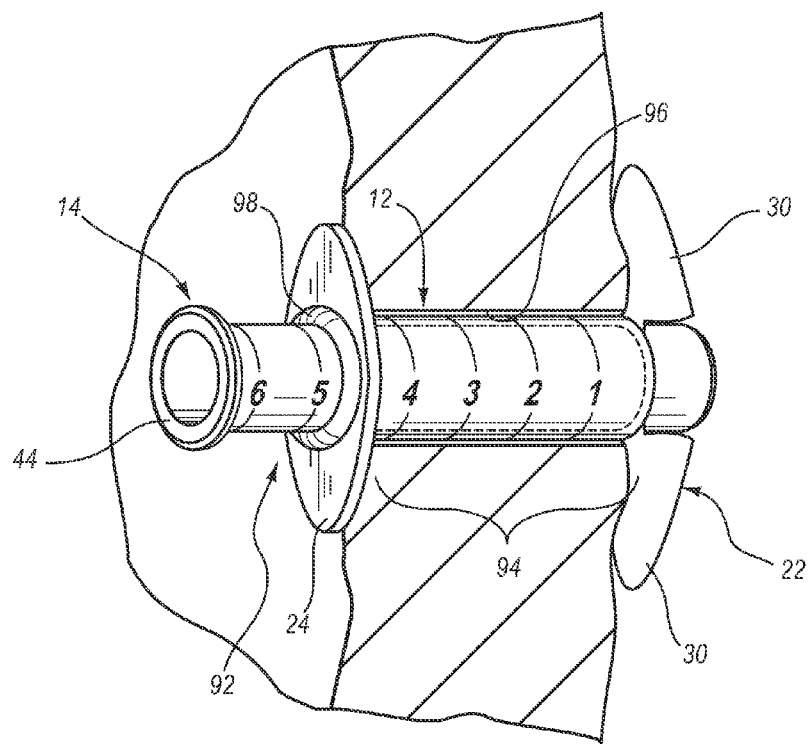

FIGS. 11A and 11B show that one embodiment of the present invention enables the internal bolster design to be employed in a stoma measuring device for measuring the length of a stoma, such as a stoma 96 shown in FIG. 11A, during feeding device replacement procedures, for instance. In particular, a measuring device 92 is shown, including a plurality of graduations 94 disposed on the bolster tube 12 so as to be visible by a user of the measuring device. During use, the measuring device 92 is inserted into the stoma 96, the internal bolster 22 deployed, and the device pulled proximally so as to seat the internal bolster against the inner entrance to the stoma, as shown in FIG. 11B. This establishes the zero point of the stoma depth. The user can then note the length of the stoma 96 by noting the number of graduation 94 of the measuring device 92 at the stoma exit site on the skin surface, thus indicating the length of the stoma 96. A second plunger stop 98 can be used in one embodiment to prevent full insertion of the plunger 14 into the cavity 20 of the bolster tube 12.

Figures 12A, 12B:
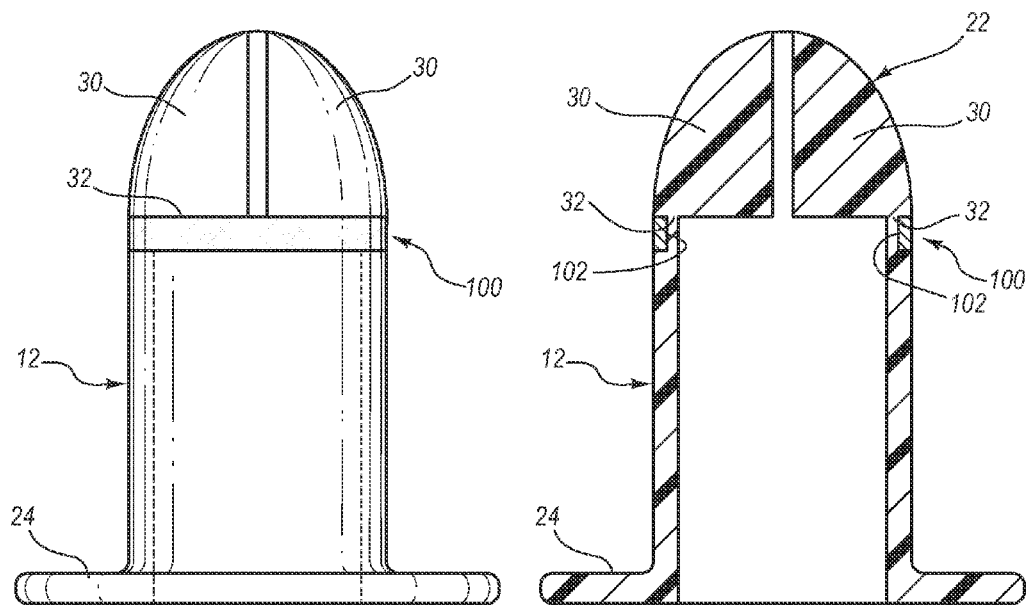
FIGS. 12A and 12B are side views of an internal bolster of the feeding device of FIG. 1A including a reinforcing collar and a notch for its positioning, according to one embodiment.

FIGS. 12A and 12B show that in one embodiment an annular reinforcing collar 100 including stainless steel or other suitably hard and biocompatible metal or substance can be added about the base of the bolster arms 30 proximate the hinge point 32 on the bolster tube 12 so as to fortify the retention force of the internal bolster 22 when deployed in a stoma. The collar 100 in one embodiment is seated in an annular notch 102 in one embodiment and as shown in FIG. 12B, though in other embodiments other reinforcement schemes can be used. For instance, the collar can be other than round to fit on bolster tubes with non-circular cross sectional shapes, or can include only a portion of a circular ring.

Figure 13A:
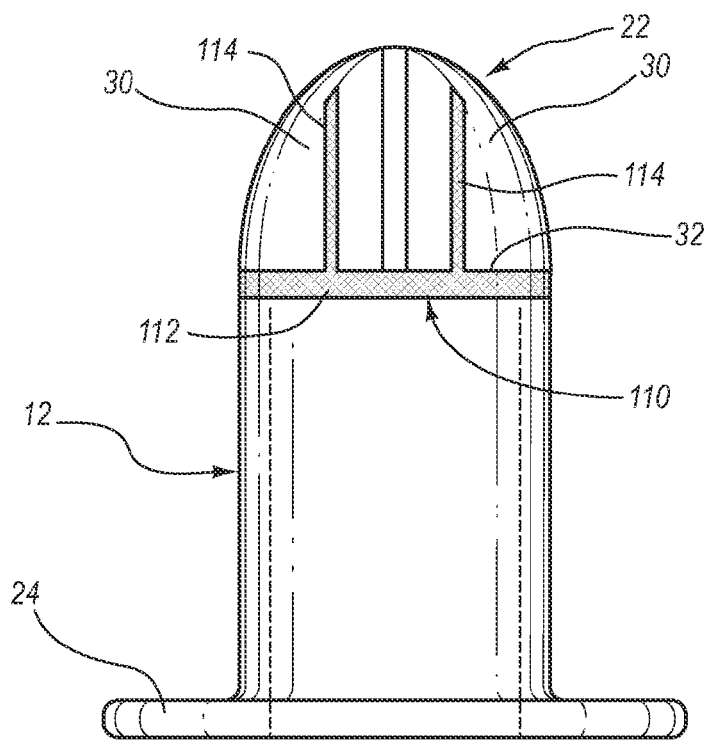
FIGS. 13A and 13B are side and end views, respectively, of an internal bolster of the feeding device of FIG. 1A including a reinforcement structure, according one embodiment.
Figure 13B:
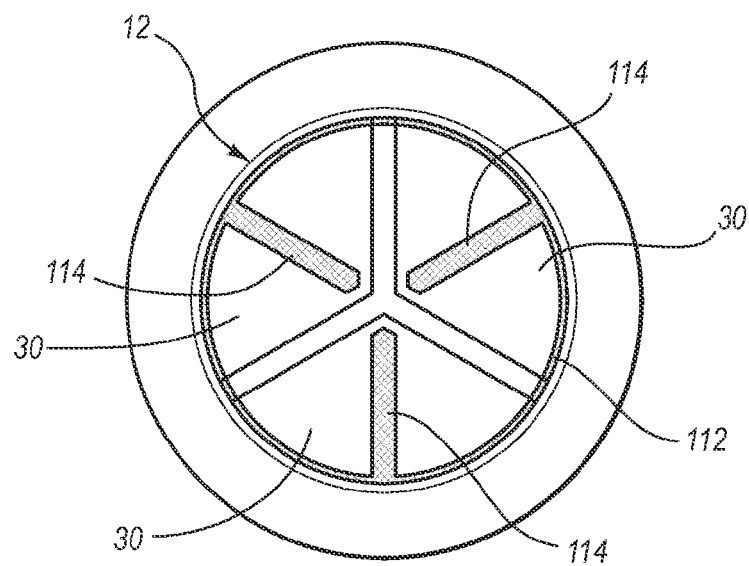

FIGS. 13A and 13B give an example of another reinforcement scheme according to one embodiment, wherein a reinforcement structure 110 includes a collar 112 similar to that shown in FIG. 12A and a plurality of spines 114 that each extend into one of the bolster arms 30 so as to provide added strength to the internal bolster 22. The spines 114 are bendable at the point of connection with the collar 112 in the present embodiment to enable pivoting of each bolster arm 30 about the hinge point 32. Stainless steel or other suitable material can be used for the collar 112 and spines 114. These and other reinforcement schemes are therefore contemplated.

Figure 14A:
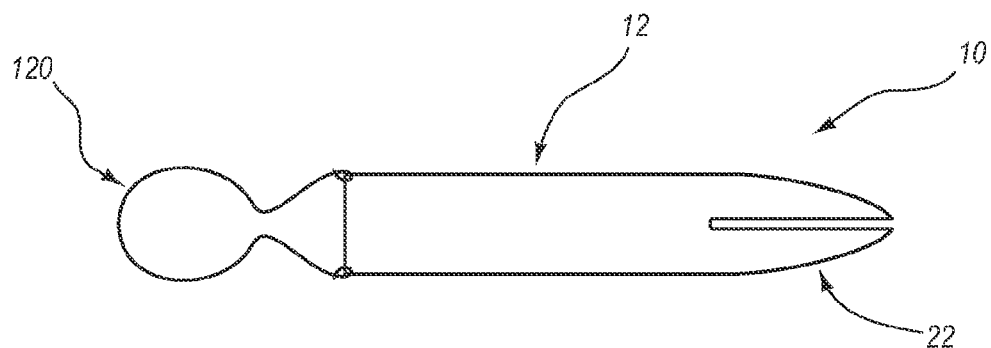
FIGS. 14A-14D are various views of a feeding device configured for initial endoscopic placement, according to one embodiment.
Figure 14B:
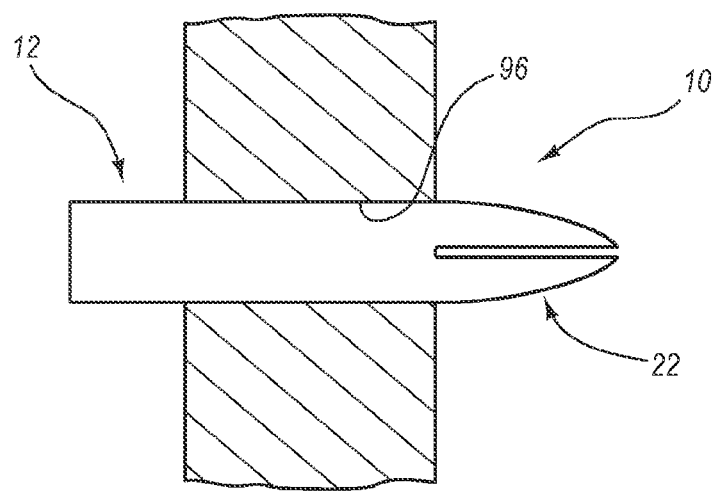
Figure 14C:
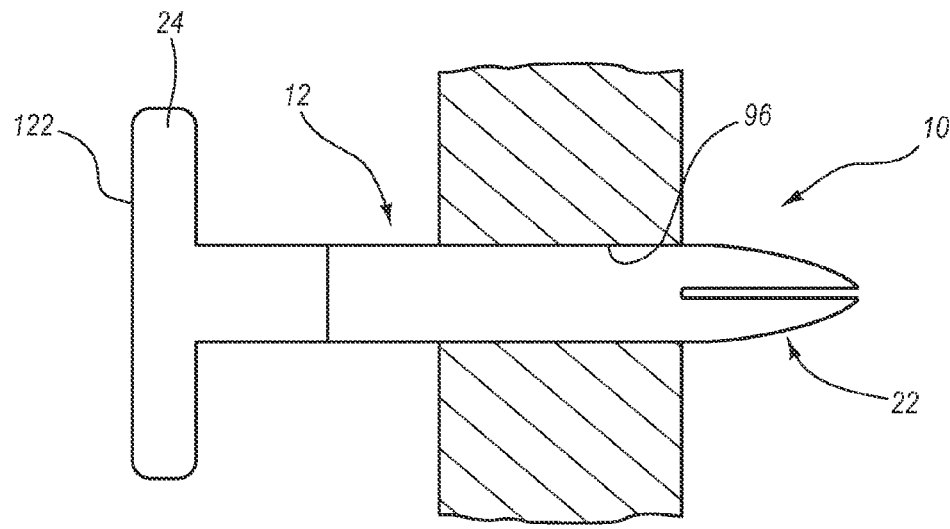
Figure 14D:
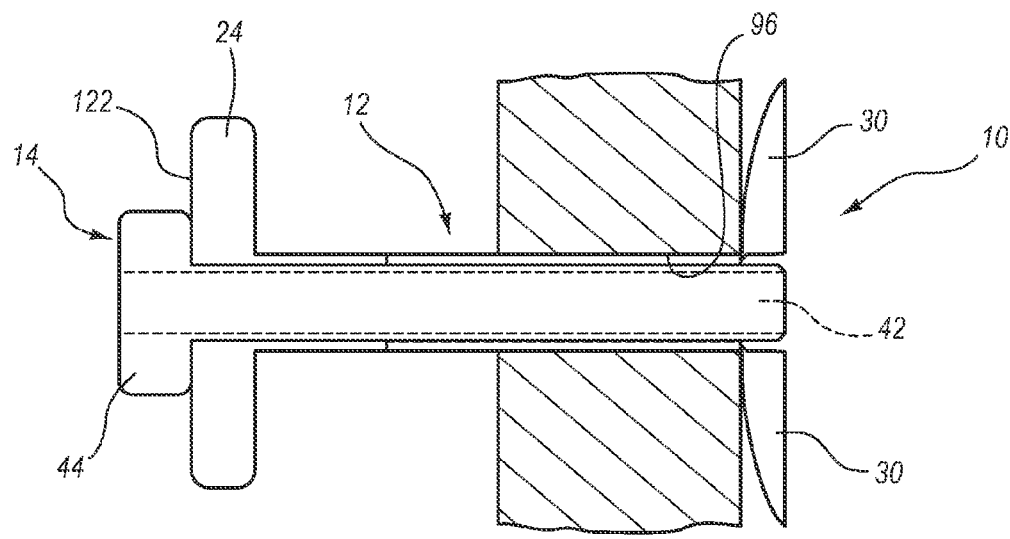
Figure 15:
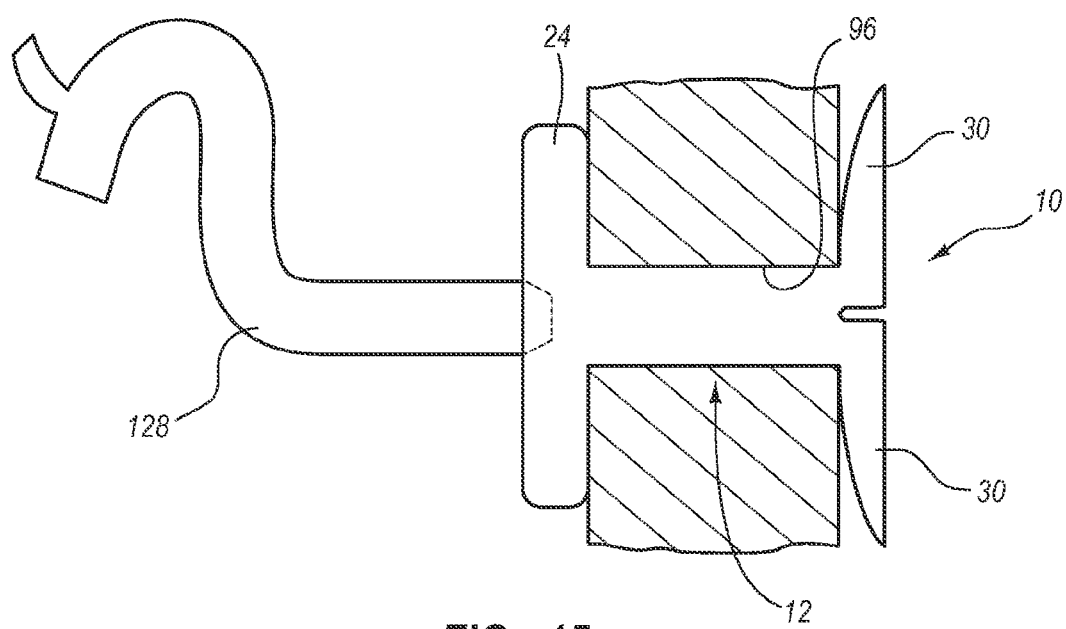
FIG. 15 is a side view of a tubing extension for providing enteral nutrition to a patient that can be employed with a feeding device such as that shown in FIG. 1A in accordance with one embodiment.

Reference is now made to FIGS. 14A-14D. In previous embodiments the internal bolster was contemplated for use, among other things, in connection with a replacement feeding device, i.e., a device replacing another device that was previously disposed within a stoma. In one embodiment, the feeding device 10 can also be configured as an initial placement feeding device for initial insertion into a patient. So configured, the feeding device 10 includes a snare 120 on the proximal end of the bolster tube 12, which snare can be removed after the bolster tube has been endoscopically inserted into the patient and positioned within the stoma 96, as shown in FIG. 14B. An adapter 122 is then attached to the proximal end of the bolster tube 12, which includes the flange 24, as shown in FIG. 14C. The plunger 14 can then be inserted into the bolster tube cavity 20 to engage and deploy the internal bolster 22, as shown in FIG. 14D. In one embodiment, it is appreciated that the adapter 122 and the plunger 14 can be connected to or integrated with one another so as to be attachable as a unit to the bolster tube 12. FIG. 15 shows that in one embodiment, the feeding device 10 can attach to, or have integrally formed therewith, an external extension tube 128 for use with enteral feeding.

Figure 16A:
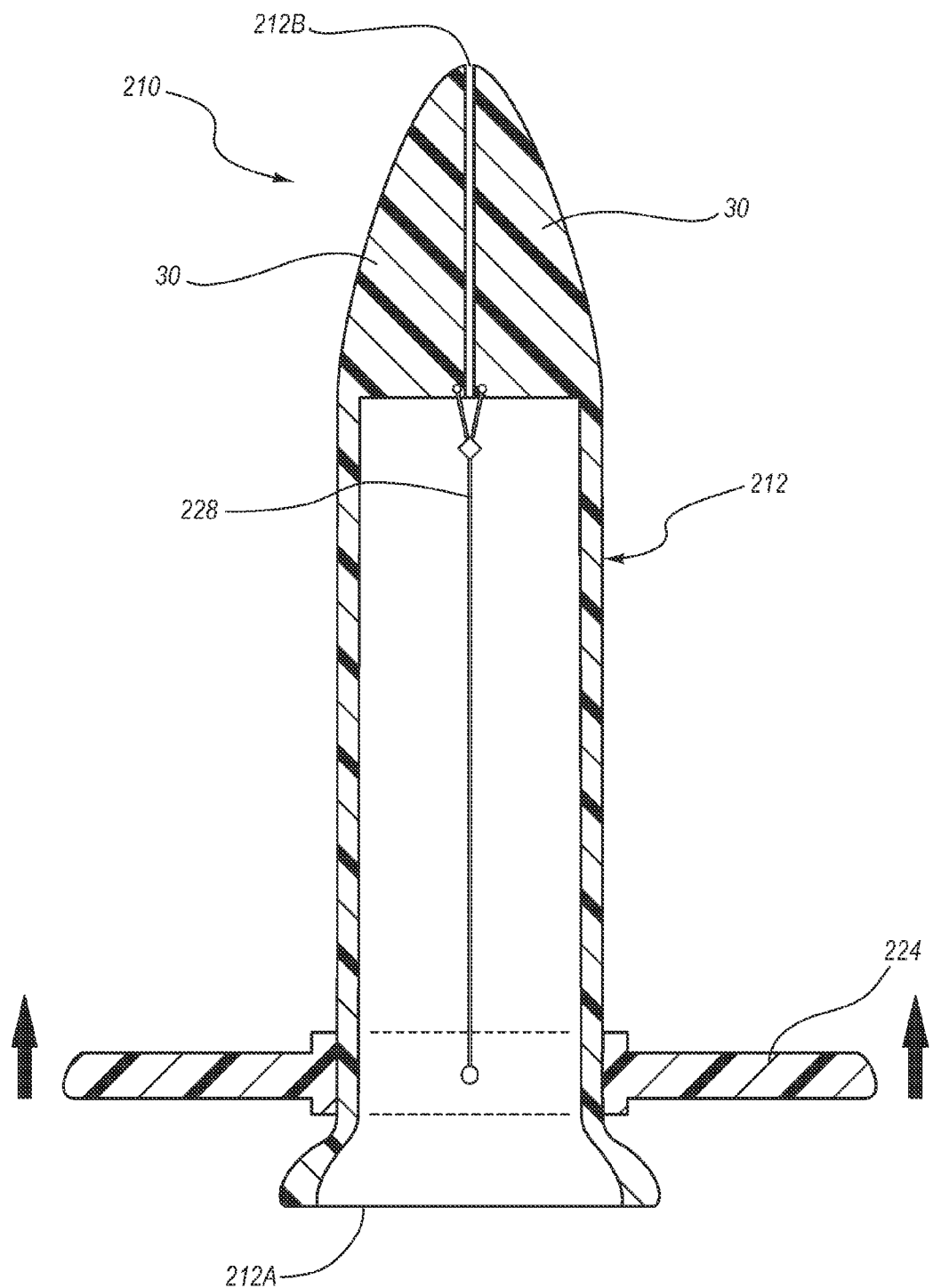
FIGS. 16A and 16B are cross sectional views of a feeding device including an internal bolster configured in accordance with one embodiment.

Reference is now generally made to FIGS. 16A-17C, which depict other examples of means for selectively moving bolster arms of an internal bolster between the first and second positions in order to selectively deploy the internal bolster for securing an indwelling medical device. In particular, FIGS. 16A and 16B depict a feeding device 210 with an extensible internal bolster according to one embodiment. The feeding device 210 includes a hollow body 212 defining a proximal end 212A and a distal end 212B. A flange 224 is attached to the body 212 and is slidable with respect thereto. Wires 228 are attached to the flange 224 and extend along the body so as to operably attach to a respective one of the extensible bolster arms 30, which are attached to the body at a hinge point via living hinges or other suitable connective scheme. The wires 228 can include a nickel-titanium alloy commonly known as nitinol, or other suitable metal or material.

Figure 16B:
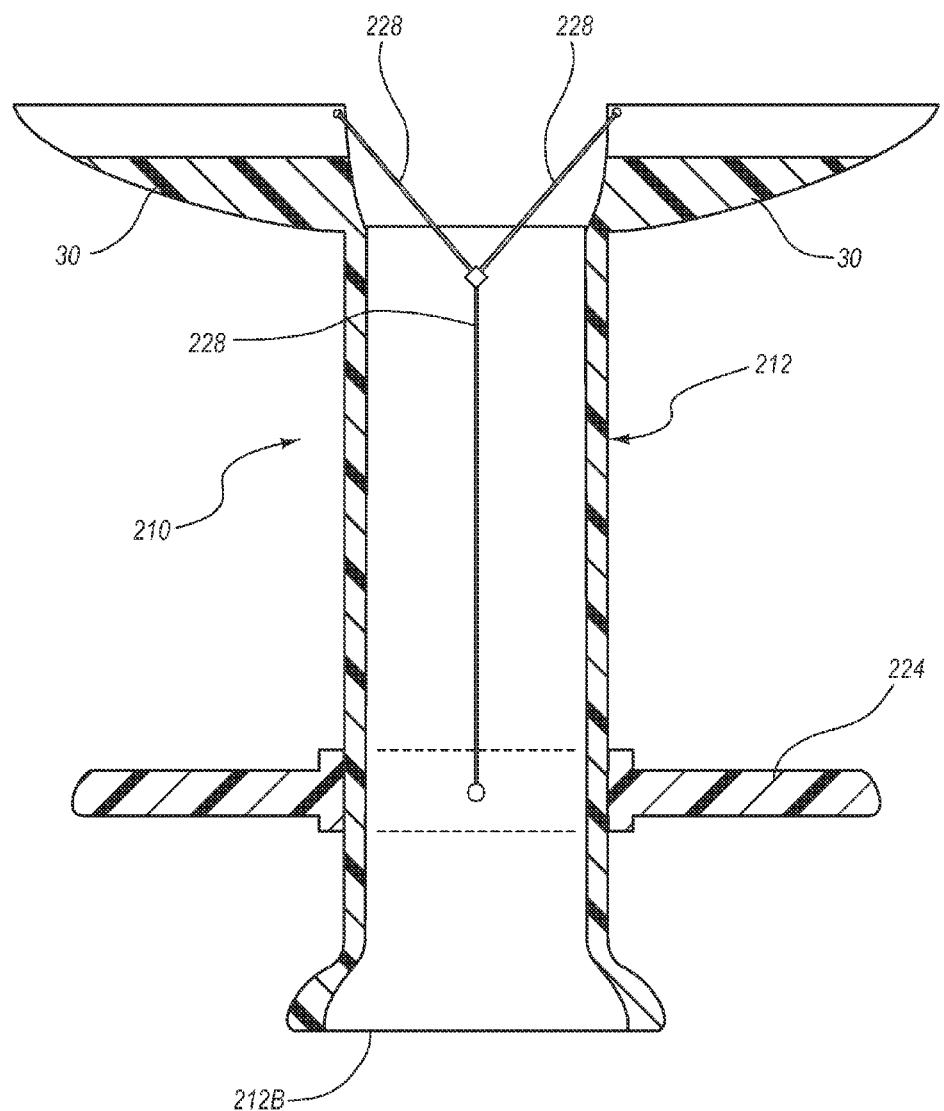

As shown in FIG. 16B, the flange 224 acts as a trigger for deploying the bolster arms 30, wherein sliding or other movement of the flange toward the distal end 212B of the body 212 causes the wires 228 to actuate the bolster arms and extend them into their deployed position. Note that the wires 228 are sufficiently rigid to actuate the bolster arms. It is further appreciated that other structures can be used to interconnect the bolster arms to the flange or other suitable component. Correspondingly, proximal movement of the flange 224 correspondingly causes the bolster arms 30 to contract back to their original un-deployed position. Thus, it is seen that multiple configurations exist for deployment of the internal bolster.

Figure 17A:
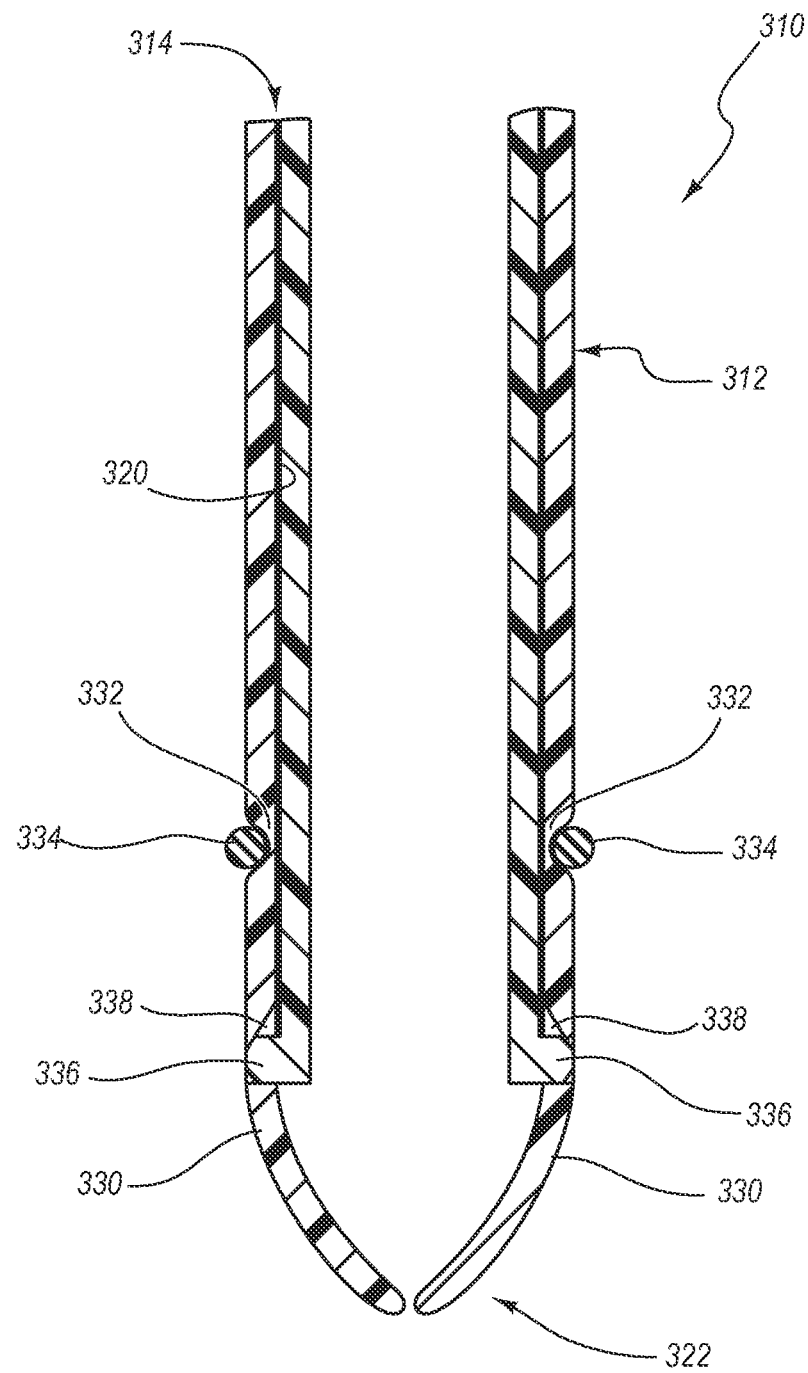
FIGS. 17A-17C are various views of a feeding device including an internal bolster configured in accordance with one embodiment.
Figure 17B:
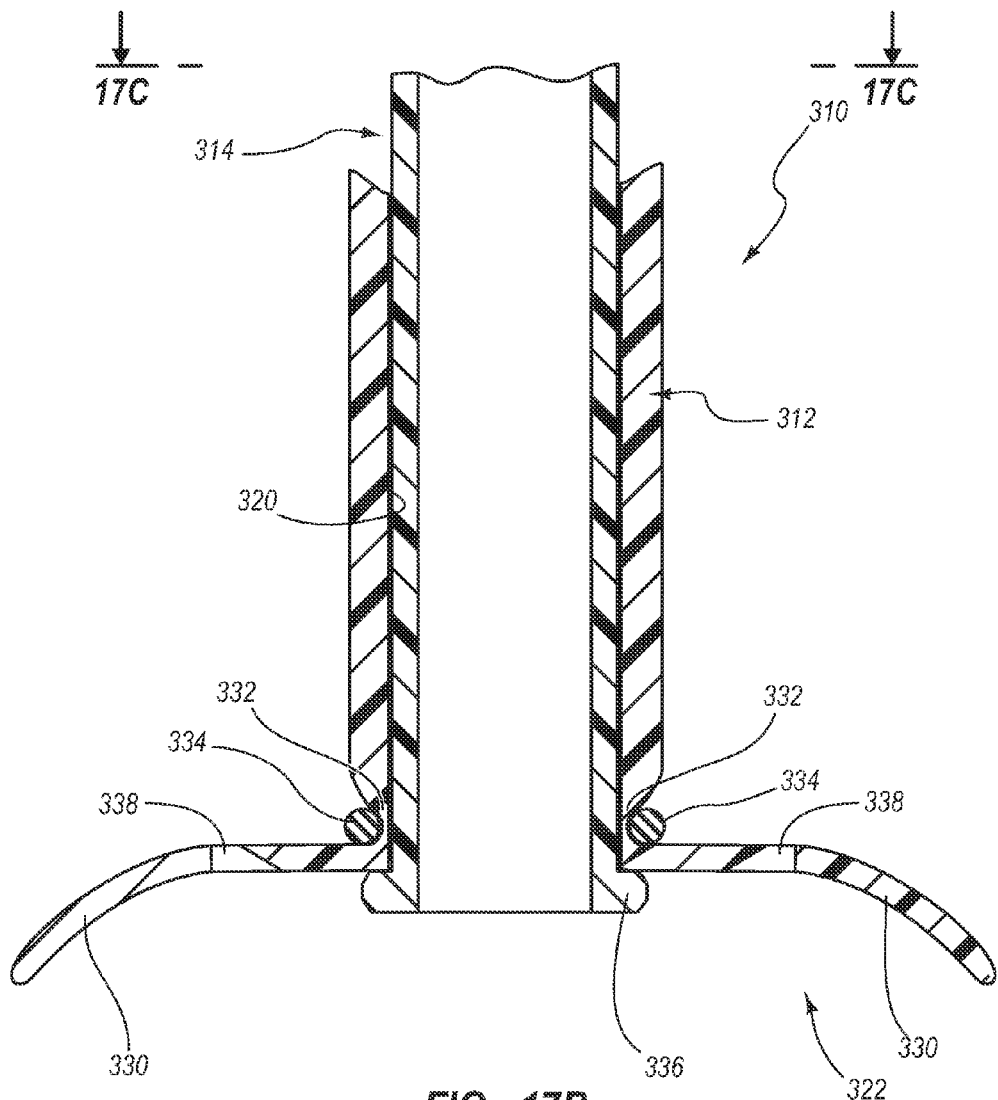
Figure 17C:
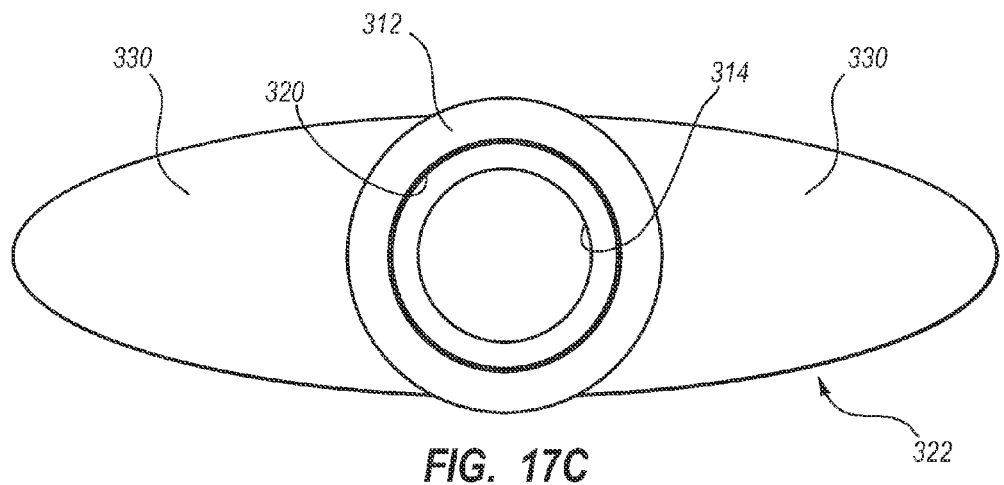

FIGS. 17A-17C depict a feeding device 310 including another example of means for selectively moving bolster arms of an internal bolster between the first and second positions, according to one embodiment. In particular, the feeding device 310 includes a bolster tube 312 that slidably receives a plunger 314 in a cavity 320 thereof, similar to previous embodiments. An internal bolster 322 is included on the distal end of the bolster tube 312, and includes two extensible bolster arms 330 attached to the bolster tube at hinge points 332 via living hinges for instance, though more or fewer arms can be employed if desired. A non-stretching O-ring 334 is positioned proximate the living hinges 332 on an outer portion of the bolster tube 312 to prevent the bolster tube from expanding in diameter during internal bolster deployment. The plunger 314 includes a radially extending annular lip 336 at its distal end.

FIG. 17A shows the feeding device 310 in a first un-deployed position, wherein the bolster arms 330 of the internal bolster 322 are un-extended. In this position, the annular lip 336 is received into an annular cutout 338 defined by each of the bolster arms 330. To deploy the internal bolster 322 from the un-deployed position shown in FIG. 17A, the plunger 314 is pulled proximally with respect to the bolster tube 312, which causes the annular lip 336 to be removed from the cutouts 338 and press against the bolster arms 330. This causes the bolster arms 330 to expand into the second deployed position shown in FIG. 17B. The O-ring 334 assists in maintaining the deployed position of the bolster arms 330. Reverse movement of the plunger 314 will correspondingly enable the annular lip 336 to re-seat within the cutouts 338 and allow the bolster arms to return to their un-deployed position, such as for insertion or removal from the stoma of a patient.

FIGS. 18A-18E depict a feeding device 410 including an extensible internal bolster according to yet another embodiment. As shown, the feeding device 410 includes a bolster tube 412 that slidably receives a plunger 414 in a cavity 420 thereof, as in previous embodiments. An internal bolster 422 is included on the feeding device 410 and includes two foldable flaps 430. The flaps 430 include a joined distal end attached to a distal end of one or more tethers 434, and a proximal end attached to a distal portion of the plunger 414. The two tethers 434 each extend from the distal end of the flaps 430 proximally to a portion of the bolster tube 412 proximal to the internal bolster 422. So configured, the flaps 430 and tethers 434 are commonly connected at a distal end of the internal bolster 422, as seen in FIGS. 18A-18E, yet respectively separated proximally therefrom so as to be independently movable with respect to one another. Note that the size, shape, and number of flaps and tethers can vary from what is explicitly shown and described herein.

Figure 18A:
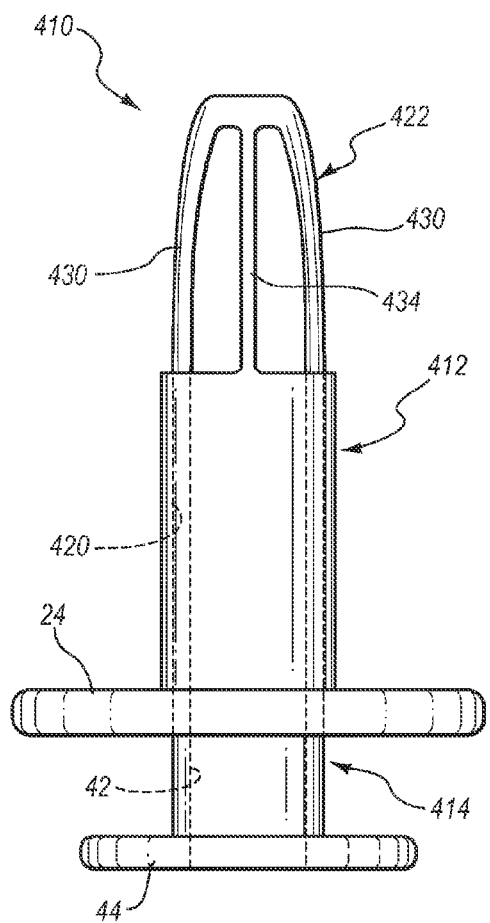
FIGS. 18A-18E are various views of a feeding device including an internal bolster configured in accordance with one embodiment.
Figure 18B:
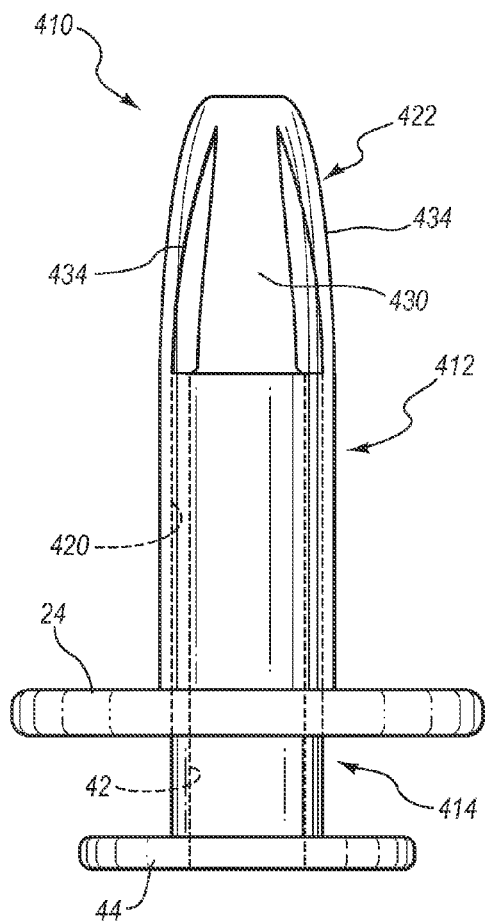
Figure 18C:
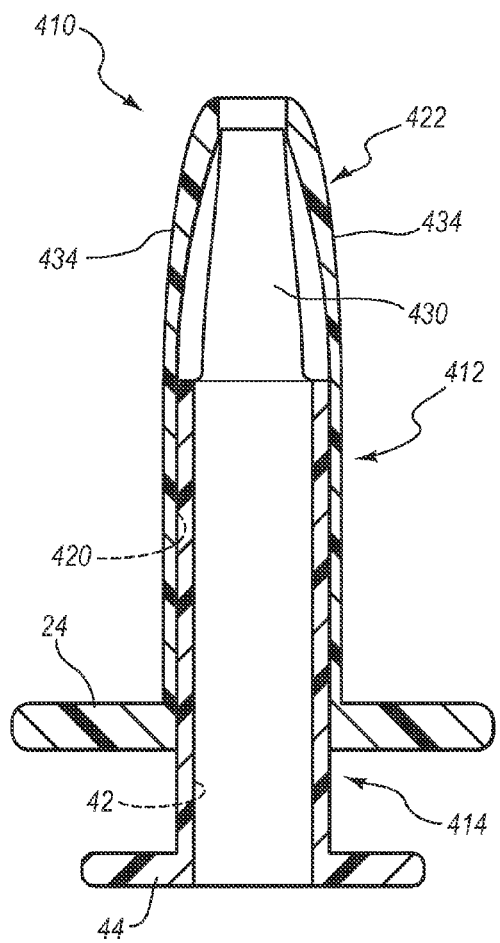
Figure 18D:
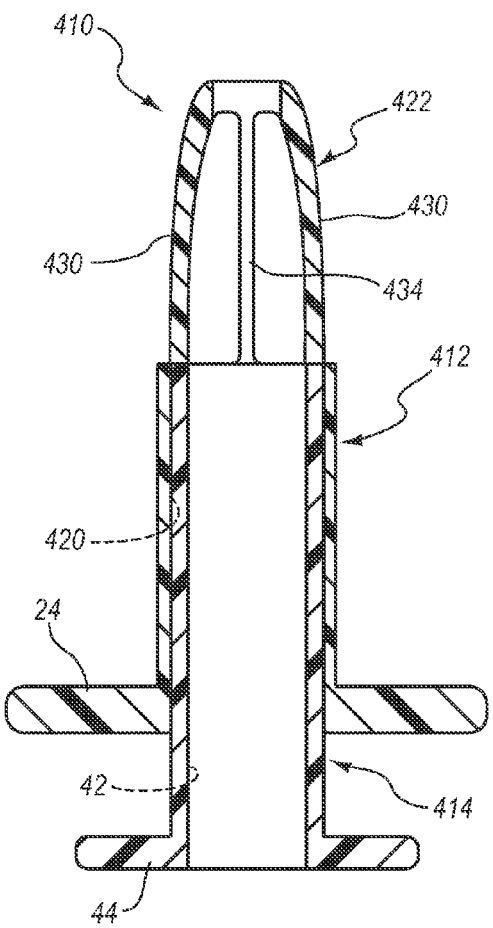
Figure 18E:
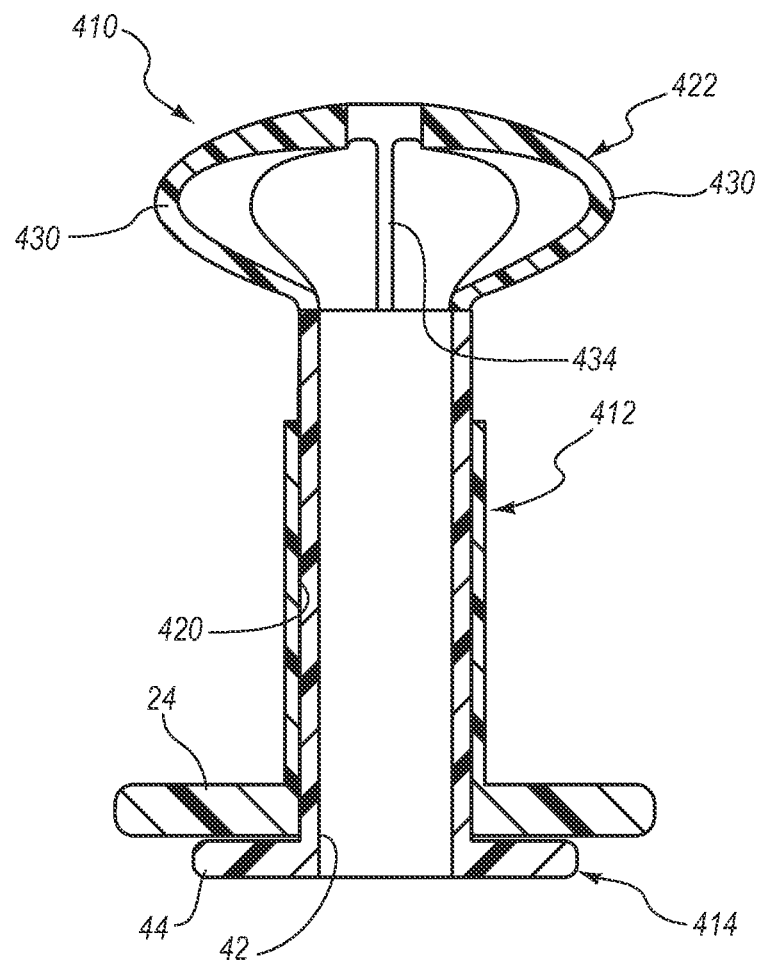

To actuate the internal bolster 422 of the feeding device 410, the plunger 414 is pushed distally. The tethers 434 prevent distal movement of the internal bolster 422 during movement of the plunger 414. This causes the flaps 430 to bend outward, as shown in FIG. 18E, thus forming an internal bolster for securing the feeding device 410 in a stoma of a patient, for instance. The process may be reversed to collapse the internal bolster 422 and remove the feeding device 410 from the patient. A suitable means for locking axial plunger movement relative to the bolster tube 412 can be included to maintain the internal bolster 422 in its deployed state.

Note that the principles described herein can be expanded while still residing within the scope of the present disclosure. For instance, the hollow plunger described above can be include other feeding channel configurations or can be other than cylindrically shaped in other embodiments.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An internal bolster for securing a medical device within a body of a patient, the internal bolster comprising:
    at least two bolster arms, each including a first end hingedly connected to a distal end of a tubular medical device and a free second end, and
    webbing disposed between adjacent bolster arms,
    wherein the at least two bolster arms are selectively deployable between a first position wherein the at least two bolster arms are substantially in-line with an axis of the medical device and a second position wherein the at least two bolster arms are substantially deflected from the axis of the medical device to enable securement of the medical device within the body.

2. The internal bolster as defined in claim 1, wherein the first end of the at least two bolster arms is hingedly connected to an outer perimeter of the distal end of the tubular medical device.

3. The internal bolster as defined in claim 2, wherein the tubular medical device further includes a plunger movable within an elongate cavity of the tubular medical device to selectively engage a base of the at least two bolster arms and reversibly deploy the at least two bolster arms from the first position to the second position.

4. The internal bolster as defined in claim 1, wherein the at least two bolster arms are positioned contiguously with one another and define a tapered atraumatic distal end of the medical device when in the first position, and wherein the bolster arms move radially outward with respect to one another in unison when deployed from the first to the second position such that the webbing can form a seal about a stoma in the body when the medical device is secured within the body.

5. The internal bolster as defined in claim 1, wherein the at least two bolster arms include a resilient material and further include a reinforcement structure to stiffen the bolster arm.

6. A medical device, comprising:
    an elongate body;
    an internal bolster, comprising a plurality of bolster arms each including a first end that is attached to a distal end of the elongate body and a free second end, each bolster arm being pivotable between a first position wherein the bolster arm is substantially parallel with the medical device body and a second deployed position wherein the bolster arm is substantially non-parallel with the medical device body; and
    a plunger that is slidable with respect to the elongate body, the plunger including a channel and an engagement surface for deploying the bolster arms from the first position to the second position, the engagement surface including a radially extending annular lip proximate a distal end of the plunger, and wherein the plunger is slid proximally such that the bolster arms are pressed between the annular lip and an O-ring disposed about the medical device so as to deploy the bolster arms radially outward to the second position.

7. The medical device as defined in claim 6, wherein each bolster arm is hingedly attached via a living hinge proximate a distal end of the elongate body, and wherein the bolster arms cover a distal end opening of the elongate body when in the first position, the distal end opening being at least partially uncovered when the bolster arms are in the second position.

8. The medical device as defined in claim 6, wherein the bolster arms when in the first position are contiguous with one another and together define an outer diameter that does not exceed an outer diameter of the distal portion of the medical device, and wherein the bolster arms are radially spread apart from one another when in the second position to secure the distal portion of the medical device within the body of the patient after insertion thereof.

9. A medical device, comprising:
    an elongate body;
    an internal bolster, comprising a plurality of bolster arms each including a first end that is attached to a distal end of the elongate body and a free second end, each bolster arm being pivotable between a first position wherein the bolster arm is substantially parallel with the elongate body and a second deployed position wherein the bolster arm is substantially non-parallel with the elongate body;
    a reinforcing collar disposed radially about at least a portion of the distal end of the elongate body;
    a plurality of spines that each extend into one of the plurality of bolster arms; and
    means for selectively moving the bolster arms between the first and second positions.

10. The medical device as defined in claim 9, wherein the means for selectively moving the bolster arms includes a portion external to the body of the patient for manually deploying the bolster arms from the first position to the second position and for retracting the bolster arms from the second position to the first position in preparation for removal of the medical device from the body of the patient.

11. The medical device as defined in claim 9, wherein the means for selectively moving the bolster arms includes a plunger that is slidable with respect to the elongate body, the plunger including an engagement surface for deploying the bolster arms from the first position to the second position.

12. The medical device as defined in claim 11, wherein the elongate body includes an elongate tube defining a cavity, the plunger being slidable within the cavity of the elongate tube, and wherein the medical device further comprises means for locking axial movement of the plunger relative to the elongate tube.

13. The medical device as defined in claim 12, wherein the means for locking axial movement includes at least one extended surface included on one of the plunger and elongate tube, the at least one extended surface seating within a corresponding recess defined on one of the plunger and the elongate tube when the plunger has deployed the bolster arms to the second position.

14. The medical device as defined in claim 12, wherein the means for locking axial movement includes threads correspondingly defined on the plunger and the elongate tube, the plunger being threadably received within the cavity of the elongate tube so as to deploy the bolster arms to the second position.

15. The medical device as defined in claim 12, wherein the means for locking axial movement includes at least one pin insertable through the elongate tube to engage the plunger so as to prevent movement thereof.

16. The medical device as defined in claim 9, wherein the means for selectively moving the bolster arms includes at least one elongate wire member interconnecting each of the bolster arms with a movable trigger external to the body of the patient, wherein movement of the trigger causes the wire member to reversibly deploy the bolster arms from the first position to the second position.

17. A method for inserting a medical device into a body of a patient, comprising:
    inserting a distal portion of the medical device into the body through a stoma, the distal portion including an internal bolster, the internal bolster including at least two bolster arms hingedly connected at a first end to the distal portion of the medical device and including a free second end, the at least two bolster arms including webbing between adjacent bolster arms and being in a first position during insertion wherein the at least two bolster arms are substantially parallel with a longitudinal axis of the medical device; and
    radially deploying the at least two bolster arms to a second position wherein the at least two bolster arms are positioned substantially non-parallel with respect to the longitudinal axis of the medical device to secure the distal portion of the medical device within the body, the webbing forming a seal about the stoma when the at least two bolster arms are deployed to the second position.

18. The method for inserting the medical device as defined in claim 17, wherein radially deploying the at least one bolster arm further comprises radially extending each of a plurality of bolster arms about a hinge point to the non-parallel second position.

19. The method for inserting the medical device as defined in claim 17, wherein the medical device includes a stoma measuring device including graduations so as to enable a measurement of a length of a the stoma through which the medical device is inserted.

20. A medical device, comprising
    an elongate body defining a cavity and including a distal portion for insertion into a body of a patient;
    a plunger movably disposed within the cavity of the elongate body; and
    an internal bolster including:
        at least one foldable flap including a proximal end attached to a distal portion of the plunger; and
        at least one tether connecting the distal portion of the elongate body with a distal end of the at least one foldable flap,
    wherein movement of the plunger within the cavity of the elongate body causes folding of the flap from a first unfolded position to a second folded position so as to enable the internal bolster to secure the distal portion of the medical device within the body of the patient.

21. The internal bolster as defined in claim 1, wherein the webbing is folded.

22. A medical device, comprising:
    an elongate body;
    an internal bolster, comprising a plurality of bolster arms each including a first end that is attached to a distal end of the elongate body and a free second end, each bolster arm being pivotable between a first position wherein the bolster arm is substantially parallel with the elongate body and a second deployed position wherein the bolster arm is substantially non-parallel with the elongate body;
    a reinforcing collar disposed radially about at least a portion of the distal end of the elongate body; and
    means for selectively moving the bolster arms between the first and second positions, including a portion external to the body of the patient for manually deploying the bolster arms from the first position to the second position and for retracting the bolster arms from the second position to the first position in preparation for removal of the medical device from the body of the patient.

23. A medical device, comprising:
    an elongate body;
    an internal bolster, comprising a plurality of bolster arms each including a first end that is attached to a distal end of the elongate body and a free second end, each bolster arm being pivotable between a first position wherein the bolster arm is substantially parallel with the elongate body and a second deployed position wherein the bolster arm is substantially non-parallel with the elongate body;
    a reinforcing collar disposed radially about at least a portion of the distal end of the elongate body; and
    means for selectively moving the bolster arms between the first and second positions, including a plunger that is slidable with respect to the elongate body, the plunger including an engagement surface for deploying the bolster arms from the first position to the second position.

24. A medical device, comprising:
    an elongate body;
    an internal bolster, comprising a plurality of bolster arms each including a first end that is attached to a distal end of the elongate body and a free second end, each bolster arm being pivotable between a first position wherein the bolster arm is substantially parallel with the elongate body and a second deployed position wherein the bolster arm is substantially non-parallel with the elongate body;
    a reinforcing collar disposed radially about at least a portion of the distal end of the elongate body; and
    means for selectively moving the bolster arms between the first and second positions, including at least one elongate wire member interconnecting each of the bolster arms with a movable trigger external to the body of the patient, wherein movement of the trigger causes the wire member to reversibly deploy the bolster arms from the first position to the second position.

* * * * *